US006919092B2

(12) United States Patent
Guittard et al.

(10) Patent No.: US 6,919,092 B2
(45) Date of Patent: Jul. 19, 2005

(54) METHOD FOR THE MANAGEMENT OF INCONTINENCE

(75) Inventors: George V. Guittard, Cupertino, CA (US); Francisco Jao, San Jose, CA (US); Susan M. Marks, San Jose, CA (US); David J. Kidney, Palo Alto, CA (US); Fernando E. Gumucio, San Jose, CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/785,805

(22) Filed: Feb. 16, 2001

(65) Prior Publication Data

US 2001/0005728 A1 Jun. 28, 2001

Related U.S. Application Data

(63) Continuation of application No. 09/280,309, filed on Mar. 29, 1999, now Pat. No. 6,262,115, which is a continuation-in-part of application No. 08/806,773, filed on Feb. 26, 1997, now Pat. No. 5,912,268, which is a continuation-in-part of application No. 08/706,576, filed on Sep. 5, 1996, now Pat. No. 5,840,754, which is a continuation-in-part of application No. 08/445,849, filed on May 22, 1995, now Pat. No. 5,674,895.

(51) Int. Cl.$^7$ ............................................. A61K 9/20
(52) U.S. Cl. ..................... 424/464; 424/468; 514/534; 514/579; 514/646; 514/663; 514/727; 514/729; 514/730
(58) Field of Search ................................ 424/464, 468, 424/474, 475, 479, 480, 484, 486; 514/534, 579, 646, 663, 727, 729, 730

(56) References Cited

U.S. PATENT DOCUMENTS

| | | | |
|---|---|---|---|
| 2,799,241 A | 7/1957 | Wurster | 118/24 |
| 2,996,431 A | 8/1961 | Barry | 167/82 |
| 3,139,383 A | 6/1964 | Neville | 167/83 |
| 3,811,444 A | 5/1974 | Heller et al. | 128/260 |
| 3,845,770 A | 11/1974 | Theeuwes et al. | 128/260 |
| 3,916,899 A | 11/1975 | Theeuwes et al. | 128/260 |
| 3,962,414 A | 6/1976 | Michaels | 424/19 |
| 3,992,518 A | 11/1976 | Chien et al. | 424/22 |
| 4,063,064 A | 12/1977 | Saunders et al. | 219/121 |
| 4,066,747 A | 1/1978 | Capozza | 424/78 |
| 4,070,347 A | 1/1978 | Schmitt | 260/77.5 |
| 4,079,038 A | 3/1978 | Choi et al. | 260/47 |
| 4,083,949 A | 4/1978 | Benedikt | 424/19 |
| 4,088,864 A | 5/1978 | Theeuwes et al. | 219/121 |
| 4,093,709 A | 6/1978 | Choi et al. | 424/19 |
| 4,111,202 A | 9/1978 | Theeuwes et al. | 128/260 |
| 4,285,987 A | 8/1981 | Ayer et al. | 427/3 |
| 4,327,725 A | 5/1982 | Cortese et al. | 128/260 |
| 4,434,153 A | 2/1984 | Urquhart | 424/22 |
| 4,612,008 A | 9/1986 | Wong et al. | 604/892 |
| 4,721,613 A | 1/1988 | Urquhart | 424/19 |
| 4,752,470 A | 6/1988 | Mehta | 424/458 |
| 4,783,337 A | 11/1988 | Wong et al. | 424/468 |
| 4,800,098 A | 1/1989 | Galland | 128/260 |
| 4,816,263 A | 3/1989 | Ayer et al. | 424/468 |
| 4,824,675 A | 4/1989 | Wong et al. | 424/438 |
| 4,853,229 A | 8/1989 | Theeuwes | 424/455 |
| 4,863,456 A | 9/1989 | Stephens et al. | 604/892.1 |
| 4,902,514 A | 2/1990 | Barclay et al. | 424/473 |
| 5,399,359 A | 3/1995 | Baichwal | 424/464 |
| 5,674,895 A * | 10/1997 | Guittard et al. | 514/534 |
| 5,811,126 A | 9/1998 | Krishnamurthy | 424/498 |
| 5,840,754 A * | 11/1998 | Guittard et al. | 514/534 |
| 5,912,268 A * | 6/1999 | Guittard et al. | 514/534 |
| 6,124,355 A * | 9/2000 | Guittard et al. | 514/534 |
| 6,262,115 B1 | 7/2001 | Guittard et al. | 514/534 |

FOREIGN PATENT DOCUMENTS

| | | |
|---|---|---|
| WO | WO 96/12477 | 5/1996 |
| WO | WO 96/37202 | 11/1996 |

OTHER PUBLICATIONS

Abdou, H.M., "Dissolution," Remington's Pharmaceutical Sciences, 17$^{th}$ Ed., 1985, Chapter 35, 653–666.

Anderberg, E.K., et al., "Physicochemical aspects of drug release—X. Investigation of the applicability of the cube root law for characterization of the dissolution rate of fine particulate materials," International Journal of Pharmaceutics, 1990, 62, 143–151.

Enomoto, et al., "Sustained release formulations containing oxybutynin chloride," Chemical Abstracts, Apr. 4, 1994, 120(14), 173491.

Enomoto, et al., "Sustained release preparation of oxybutynin chloride," Chemical Abstracts, May 2, 1994, 120(18), 227011.

Grafton, P., "General principles for designing with plastics," Modern Plastics Encyclopedia, Oct. 1969, 46(10A), 62–70.

Nisson, C.G., et al., "Comparison of a 10–mg controlled release oxybutynin tablet with a 5–mg oxybutynin tablet in incontinent patients," Neurology & Urodynamics, 1997, XP002099745, 16, 533–542.

The United States Pharmacopeia/The National Formulary, "Dissolution," USP XXII, NF XVII, Jan. 1, 1990, 711, 1578–1579.

The United States Pharmacopeia/The National Formulary, "Dissolution," USP 23/NF18, Jan. 1, 1995, 711, 1791–1796.

The United States Pharmacopeia/The National Formulary, "Test solutions," UPS 23/NF 180, Jan. 1, 1995, 2052–2053.

(Continued)

Primary Examiner—Shelley A. Dodson
Assistant Examiner—Konata M George
(74) Attorney, Agent, or Firm—Woodcock Washburn LLP

(57) ABSTRACT

A composition and a dosage form are disclosed comprising oxybutynin alone/or accompanied by another drug indicated for therapy. A method is disclosed for administering oxybutynin alone/or accompanied by a different drug or for administering oxybutynin and a different drug according to a therapeutic program for the management of incontinence alone, and for other therapy.

23 Claims, No Drawings

OTHER PUBLICATIONS

Kodama, K.K., "Sustained release preparation of oxybutynin chloride—comprises oxybutynin chloride, acidic substance, gelling agent and higher alcohol," *Database WPI, Derwent Publication Ltd., London, GB*, AN 94–068306, XP002096606, Jan. 18, 1994, 1 page.

Kodama, K.K., "Pharmaceutical preparations for prolonged action against urinary incontinence—comprise sustained release oxybutynin chloride for pharmaceutical compsn. sustained release coating film on non water soluble polymers and/or ethylcellulose," *Database WPI, Derwent Publication Ltd, London, GB*, AN 94–031722, XP002096607, Dec. 21, 1993, 1 page.

Gupta, S. K. et al. "Evidence of Site–Specific Presystemic Methabolism of Oxybutynin Following Oral Administration," *Clinical Pharmacology & Therapeutics*, vol. 61, No. 2, 1997, P. 227 XP002096606.

Lu, S. M., Yu, Y. J. "Dimensionless Presentation for Drug Release from a Coated Pure Drug Bead: 2 Experiment," Inter. J. Of Pharm., vol. 112, pp. 117–124 (1994).

Remington's Pharmaceutical Sciences, 14$^{th}$ Ed., pp. 1626–1628 (1970).

Fincher, J. "Particle Size of Drug and Its Relationship to Absorption and Activity," Journal of Pharmaceutical Sciences, vol. 57, No. 11, pp. 1825–1835 (1986).

Remington's Pharmaceutical Sciences, 17$^{th}$ Ed., pp. 1603–1625 (1985).

Rosoff, M. "Polymers and Aggregate Systems," *Controlled Release of Drugs*, Chapter 2, pp. 53–95 (1989).

Coleman, M. et al., "A practical Guide to Polymer Miscibility," *Polymer Reviews*, vol. 31, pp1187–1231 (1990).

Roerdink et al., "Drug Carrier Systems," vol. 9, pp. 57–109 (1989).

Leong et al., "Polymeric Controlled Drug Delivery," vol. 1, pp. 199–233 (1987).

Roff et al., "Handbook of Common Polymers," published by CRC Press (1971).

Chemical Abstracts, vol. 120, No. 18, May 2, 1994, Abstract No. 227011.

Chemical Abstracts, vol. 120, No. 14, Apr. 4, 1994, Abstract No. 173499.

"General principles for designing with plastics" by P. Grafton, 1969–1970 Modern Plastics Encyclopedia, vol. 46, pp 62–70.

"Preparation of Compressed Tablet Granulations by the Air–Suspension Technique II" by Dale E. Wurster, J. of Amerc. Phar. Association Vol. 49 No. 2, pp 82–84.

"Air–Suspension Technique of Coating Drug Particles" by Dale E. Wurster, J. Am Phar. Assoc. Sci. Ed., vol. 48, pp. 451454, Aug. 1959.

Pharmaceutical Science, by Remington, 14th Ed., pp 1626–1979, (1970).

* cited by examiner

METHOD FOR THE MANAGEMENT OF INCONTINENCE

CROSS-REFERENCE TO RELATED APPLICATION

This application is a continuation of U.S. patent application Ser. No. 09/280,309, filed Mar. 29, 1999, now U.S. Pat. No. 6,262,115, which is a continuation-in-part of U.S. patent application Ser. No. 08/806,773 filed Feb. 26, 1997 now U.S. Pat. No. 5,912,268, which application is a continuation-in-part of U.S. patent application Ser. No. 08/706,576 filed Sep. 5, 1996, now U.S. Pat. No. 5,840,754 issued Nov. 24, 1998, which is a continuation-in-part of U.S. patent application Ser. No. 08/445,849 filed May 22, 1995, now U.S. Pat. No. 5,674,895 issued Oct. 7, 1997, benefit is claimed of these applications, that are assigned to the ALZA Corporation of Palo Alto, Calif.

FIELD OF THE INVENTION

This invention pertains to the management of incontinence. More specifically the invention relates to the management of incontinence by administering to a patient having the symptoms of incontinence a therapeutically effective dose of oxybutynin alone, in combination with another drug, proceeded by the administration of another drug, or followed by the administration of another drug.

BACKGROUND OF THE INVENTION

Many people are affected by urinary incontinence. Incontinence is particularly common in the elderly, urinary incontinence is present in approximately fifty percent of nursing home patients, and urinary incontinence is a well known urologic problem in women. It will affect nearly all women in some form during their lifetime, and it is of significant medical and social concern to all humans who experience it. Urinary incontinence arises from the anatomy and from the physiology of the urinary tract, which is composed of a bladder and a sphincter. Anatomically, the bladder consists of the bladder musculature, also known as detrusor, and the trigone. The sphincter includes the bladder neck and the proximal urethra. The detrusor muscle is innervated by the pelvic nerve through the parasympathetic nervous system, and the bladder neck and proximal urethra are innervated by the sympathetic nervous system.

The major functions of the bladder are the storage and expulsion of urine. The bladder is responsible for accommodating increasing volumes of urine at low pressures. Normally, the bladder remains closed during bladder filling and continence is maintained as long as the bladder neck and urethral pressure exceeds intravesical pressure. Voluntary voiding occurs when intravesical pressure exceeds bladder neck and urethral pressure, and involuntary voiding also known as involuntary incontinence occurs when the travesical pressure exceeds the bladder neck and urethral pressure. Involuntary incontinence also known as urge incontinence and overactive bladder, occurs with a loss of a large volume of urine accompanied by symptoms of urgency, frequency and nocturia caused by an unstable bladder or detrusor instability. The patient may lose urine with a change in position or with auditory stimulation. The loss of small volumes of urine usually occurs because bladder overdistension by a large amount of residual urine referred to as overflow incontinence. Urinary incontinence is also known as overactive bladder with symptoms of urinary frequency or urge incontinence.

The present management of incontinence consists in administering a smooth muscle relaxant, such as oxybutynin, which acts directly on the smooth muscle at the site distal to the cholinergic receptor. The prior art administered oxybutynin alone for this stated therapeutic purpose. The prior art usual dose for the pharmacologic management of incontinence is repeated, nonsustained and noncontrolled doses from two-to-four times a day for oxybutynin. The prior art administered separately the steriods, estrogen and/or progesterone hormone replacement therapy however, this steroid therapy is insufficient for the management of incontinence.

In light of the above presentation it will be appreciated by those versed in the medical and pharmaceutical dispensing arts to which this invention pertains that a pressing need exists for a therapeutic method that can deliver the therapeutic drug oxybutynin in a controlled, sustained-extended dose to a patient in clinical need of incontinence management. The pressing need exists for an oral method of therapy that can deliver oxybutynin alone at a substantially sustained release constant dose per unit time for its therapeutic effect. The need exists additionally for a method for delivering a dose of oxybutynin once-a-day, when indicated, for its intended therapy while avoiding an overdose and for lessening the side effects that can accompany the drug. The pressing need exists further for a method that can administer oxybutynin in combination with another and different drug, or in different therapeutic programs for the management of incontinence and for the management of health and disease.

It will be appreciated by those skilled in the medical and pharmaceutical arts to which this invention pertains, that if a novel and unique method of administration is made available that delivers oxybutynin alone, or in combination with another drug in a therapeutically effective dose over a sustained time for the management of incontinence, while lessening the incidence of over and under dose, such a method of therapy would represent an advancement and a valuable contribution for providing practical therapy.

SUMMARY OF THE INVENTION

According to the invention, it is an object of the invention to provide a method for the management of urinary incontinence with oxybutynin and/or its pharmaceutically acceptable salt alone, or in combination with another drug, or preceeded by or followed by the administration of another drug, for the management of incontinence in human male and female patients. The object of the invention further comprises a method for administering oxybutynin alone, and/or in combination with or preceded by or followed by an estrogen and/or a progestin for treating urinary incontinence in pregnant, nonpregnant, postpartum, menopause, post menopausal, and during climaterix period of change occurring in the transition to menopause in a patient in need of therapy.

DETAILS OF THE INVENTION

The scientific terms and scientific phrases used in this specification embrace the following definitions: Dosage form denotes a drug delivery system for administering a therapeutically effective dose of drug, for example oxybutynin to a patient in need of therapy. The dosage form may be administered once-daily, that is, as a once-a-day dosage form for increasing patient compliance for treating overactive bladder, or more frequently as indicated by a physician, for example twice-daily or thrice-daily. Sustained release denotes the constant delivery of drug for up to twenty-hours. Controlled release denotes the delivery of the drug at a rate controlled by a dosage form by the method of the invention.

Zero-order release denotes the method of delivery of drug at a uniform rate to dampen the peaks and valleys observed in non-zero order method of drug delivery. Therapeutically effective amount denotes the dose of delivered drug sufficient to provide a local or a systemic effect in a patient. Menopause denotes the period of natural cessation of menstruation in the female. Post menopausal denotes the time occurring after menopause. Pregnancy denotes the state of containing an unborn fetus within the female. Postpartum denotes the period following birth.

The present invention provides a therapeutic composition comprising 240 ng to 650 mg (nanogram to milligrams) of oxybutynin or an oxybutynin therapeutically acceptable salt. The pharmaceutically acceptable salt is selected from the group consisting of acetate, bitartrate, citrate, edetate, chloride, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate, and tartrate. The drug oxybutynin can be present as the racemate, as the R-enantiomer or as the S-enantiomer. The oxybutynin and its pharmaceutically acceptable salt can be administered at a controlled mean release rate of 0.10 ng per hour to 25 mg per hour for the management of incontinence up to 24 hours. The dosage forms provided by the invention can administer oxybutynin in doses such as 5 mg, 10 mg, 15 mg, 20 mg etc. for the management of incontinence. The oxybutynin can be administered alone, or in therapeutic programs with another and different drug, from the same dosage form or from different dosage forms.

Representative of a drug, for example a steroid, that can be administered with prior to or followed by the administration of oxybutynin, according to the method of the invention in the same or in an accompanying method, at the same or at a different time, or the drug can be administered separately within up to twenty-four hour period comprise a progestin member selected from the group consisting of progesterone, medroxyprogesterone, medroxyprogesterone acetate, hydroxyprogesterone, hydroxyprogesterone caproate, norethindrone, norethindrone acetate, megestrol, megestrol acetate, progestin, progestogin, norgestrel, norethisterone, norethisterone acetate, levonorgestrel, norgestimate, norethynodrel, 17-hydroxyprogesterone esters, 19-nor-17-hydroxyprogesterone, 19-nor-17-hydroxyprogesterone esters, 17α-ethinyltestosterone, 17α-ethinyl-19-nor-testosterone, d-17β-acetoxy-13β-ethyl-17α-ethinyl-17β-hydroxygon-4-en-3-one, 13β-ethyl-17β-hydroxygon-4-en-3-one, 13β-17α-diethyl-17β-hydroxygon-4-en-3-one, chlormadione acetate, dimethistrone, 17α-ethinyl-β-acetoxy-19-norandrost-4-en-3-one oxime, 3-ketodesogestrel, desogestrel, gestodene, and gestodene acetate. The dose of the progestin and its progrestone derivatives administered is 10 ng to 600 mg, that is administered alone, or in combination with an estrogen, and is indicated for hormone replacement therapy.

Representative of a drug that can be administered with oxybutynin according to the method of the invention, or administered separately in a separate administration in twenty-four hours include an estrogen steroid possessing estrogenic activity selected from the group consisting estradiol, estradiol valerate, estradiol benzoate, estradiol cypionate, estradiol propionate, estradiol dipropionate, estradiol acetate, ethinyl estradiol, 17α-ethinyl estradiol-esters, 17α-ethinyl estradiol acetate, 17α-ethinyl estradiol benzoate, 17α-ethinyl estradiol ethers, estrone, estrone acetate, estrone sulfate, estriol, estriol succinate, estriol triacetate, conjugated equine estrogens, and estradiol esters. The dose of estrogen and its estrogen derivatives is 10 ng to 600 mg, that is administered alone, or in combination with a progestin for hormone replacement therapy.

Representative of progestin and estrogen combination that can be administered according to the methods of this invention comprise a hormone pair selected from the group consisting of progestin and estradiol valerate, progestin and piperazine estrone, progestin and estrone, progestin and estriol, progestin and conjugated equine estrogens, progesterone and estradiol, progesterone and estrone, progesterone and estriol, progesterone and conjugated equine estrogens, norethisterone and estradiol, medoxyprogesterone and estradiol, norgestrel and estradiol, dyhrogesterone and estrogen, progestrone and estrogen sulfate, progesterone and 17α-dihydroequilin, and progesterone and equilenin.

The method of the invention provides oxybutynin and the steroids can be administered from the same dosage form, or the oxybutynin and the steroids can be administered separately from different dosage forms, with in either administrations, the oxybutynin and the steroids, in one present administration, administered within a twenty-four therapeutic period.

The method of the invention further provides delivery means for administering oxybutynin at a rate conducive for lessening the conversion of oxybutynin at least in part to the desethyl metabolite, desoxy. The method provides for the controlled and sustained rate at which oxybutynin is delivered to the plasma to lessen the circulating desoxy metabolite and to reduce side effect associated therewith. The method provides for oxybutynin delivery to a patient at a rate which gives an oxybutyninidesoxy metabolite ratio higher than 0.18:1 and/or the plasma level of the desoxy metabolite do not exceed 350 ng·h/ml, to lessen side effects. According to this feature of the invention there is provided a desethyl metabolite of α-cyclohexyl-α-hydroxy-benzeneacetic acid-4-(diethyl amino)-2-butynyl ester, or its pharmaceutically acceptable salt so the desethyl metabolite does not exceed 350 ng·h/ml, and may even exhibit peak levels of 250 or 200 ng·h/ml.

The method for delivering oxybutynin neat, and/or other drugs according to the invention comprises, in one manufacture the use of drug releasing beads that on dissolution or diffusion release the drug over 24 hours. The drug releasing beads comprise a central composition or core comprising a drug and pharmaceutically acceptable composition forming ingredients including an optional lubricant, antioxidant, and buffer. The beads are medical preparations with a general diameter of 1 mm to 2 mm. The beads comprise doses of drug, for example, 1 mg, 2 mg, 10 mg, and 20 mg, increasing up to 40 mg. The beads in an embodiment are formed of noncrossed-linked materials to enhance their discharge from the gastrointestional tract. The beads are coated with a release rate controlling polymer that give a timed released profile. The timed release beads are manufactured into a tablet for therapeutically effective drug administration. The beads are made into matrix tablets by the direct compression of a plurality of beads coated with, for example, an acrylic resin and blended with excipients such as hydroxypropyl-methylcellulose. The manufacture of beads is disclosed in *Inter. J. of Pharm.*, by Lu, Vol. 112, pp. 117–124 (1994); *Pharm. Sci.*, by Remington, 14$^{th}$ Ed. pp. 1626–1628 (1970); *J. Pharm. Sci.*, by Fincher, Vol. 57, pp. 1825–1835 (1968); and U.S. Pat. No. 4,083,949. The manufacture of the tablet is described in *Pharmaceutical Sciences*, by Remington, 17$^{th}$ Ed., Chp. 90, pp. 1603–1625, (1985), published by Mack Publishing Co., Easton, Pa.

The method for delivering oxybutynin alone, or in combination with another drug comprises in another embodiment the use of oxybutynin coated on a polymer substrate. The polymer can be an erodible, or a nonerodible polymer. The coated substrate is folded onto itself to provide a bilayer polymer drug dosage form. For example, 1 ng to 40 mg oxybutynin alone, or in combination with an estrogen, or in combination with an estrogen-progestin pair is coated onto a polymer such as a polypeptide, collagen, gelatin, polyvinyl alcohol, polyorthoester, polyacetyl, or a polyorthocarbonate, and the coated polymer folded onto itself to provide a bilaminated dosage form. In operation, the bioerodible dosage form erodes at a controlled rate to dispensed a therapeutic dose of oxybutynin alone, or oxybutynin and a steroid pair over a sustained release period. Representative biodegradable polymer comprise a member selected from the group consisting of biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly(dehydropyrans), and poly(dioxinones). The polymers are known to the art in *Controlled Release of Drugs*, Rosoff, Chp. 2, pp. 53–95 (1989); and in U.S. Pat. Nos. 3,811,444; 3,962,414; 4,066,747, 4,070,347; 4,079,038; and 4,093,709.

The method of the invention further uses a dosage form comprising a polymer that releases a drug by diffusion through a polymer, or by flux through pores, or by rupture of a polymer matrix. The drug delivery polymeric dosage form comprises a concentration of 10 ng to 250 mg homogenously contained in or on a polymer. The dosage form comprises at least one exposed surface at the beginning of dose delivery. The nonexposed surface when present is coated with a pharmaceutically acceptable material impermeable to the passage of drug. The dosage form can be manufactured by procedures known to the prior art. An example of providing a dosage form comprises blending a pharmaceutically acceptable carrier, like polyethylene glycol, with a known dose of oxybutynin alone, or oxybutynin and an estrogen, at an elevated temperature, like 37° C., and adding it to a silastic medical grade elastomer with a cross-linking agent, for example, octanoate, followed by casting in a mold. The step is repeated for each optional successive layer. The system is allowed to set, for 1 hour, to provide the dosage form. Representative polymers for manufacturing the dosage form comprise a member selected from the group consisting of olefin and vinyl polymers, addition polymers, condensation polymers, carbohydrate polymers, and silicon polymers as represented by poly (ethylene), poly(propylene), poly(vinyl acetate), poly (methyl acrylate), poly(isobutyl methacrylate), poly (alginate), poly(amide), and poly(silicone). The polymers and manufacturing procedures are known in *Polymers*, by Coleman et al., Vol. 31, pp. 1187–1231 (1990); *Drug Carrier Systems*, by Roerdink et al., Vol. 9, pp. 57–109 (1989); *Adv. Drug Delivery Rev.*, by Leong et al., Vol. 1, pp. 199–233 (1987); *Handbook of Common Polymers*, Compiled by Roff et al., (1971), published by CRC Press; and U.S. Pat. No. 3,992,518.

The method of the invention also uses a dosage form comprising a matrix comprising a plurality of tiny pills. The timed released tiny pills provide a number of individual doses for providing various timed doses for achieving a sustained-release drug delivery profile over 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic matrix comprises a plurality of 4 to 50 tiny pills, each tiny pill comprising a dose population of from 10 ng, 0.5 mg, 1 mg, 1.2 mg, 1.4 mg, 1.6 mg, 5.0 mg, etc. The tiny pills comprise a release rate controlling wall of 0.001 up to 10 mm thickness to provide for the timed release of drug. Representative of wall-forming materials include a triglyceryl ester selected from the group consisting of glyceryl tristearate, glyceryl monostearate, glyceryl dipalimitate, glyceryl laureate, glyceryl didecenoate and glyceryl tridenoate. Other wall forming materials comprise polyvinyl acetate phthalate, methylcellulose phthalate, and microporous vinyl olefins. Procedure for manufacturing tiny pills are disclosed in U.S. Pat. Nos. 4,434,153; 4,721,613; 4,853,229; 2,996,431; 3,139,383, and 4,752,470.

The method of the invention also comprises administering orally to a human patient a dosage form comprising a semipermeable wall that surrounds a therapeutic composition comprising oxybutynin. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained oxybutynin therapy. The method of the invention also uses in another embodiment an osmotic dosage form comprising a wall surrounding a compartment, the wall comprising a semipermeable polymeric composition permeable to the passage of fluid and substantially impermeable to the passage of oxybutynin present in the compartment; an oxybutynin drug layer composition in the compartment comprising the oxybutynin; a hydrogel push layer composition in the compartment comprising an osmotic formulation for imbibing and absorbing fluid for expanding in size for pushing the oxybutynin composition layer from the dosage form; and at least one passageway in the wall for releasing the oxybutynin. The method delivers the oxybutynin, alone or in combination with a steroid by imbibing fluid through the semipermeable wall at a fluid imbibing rate determined by the permeability of the semipermeable wall and the osmotic pressure across the semipermeable wall causing the push layer to expand; and thereby deliver the therapeutically active oxybutynin from the dosage form through the exit passageway to a patient over a prolonged period of time up to 24 or even 30 hours. The oxybutynin administered by the dosage form of the invention is in the therapeutic range that avoids a toxic dose and avoids an ineffective dose for antispasmodic therapy. The oxybutynin may thus be administered by the methods of this invention to patients with uninhibited neurogenic and reflex neurogenic bladder for increased vessel capacity which diminishes the frequency of uninhibited contractions of the detrusor muscle and delays the desire to void. The dosage form is indicated for the relief of symptoms associated with voiding such as urgency, urge incontinence, frequency, nocturia and incontinence in patients in neurogenic bladder. The dosage form can be used also for human hormone replacement therapy as described above.

The osmotic dosage forms in one manufacture comprise a therapeutic composition comprising 240 ng to 650 mg of a member selected from the group consisting of oxybutynin and its pharmaceutically acceptable salt, from 10 mg to 350 mg of a pharmaceutically acceptable hydrogel such as a polyalkylene oxide of 75,000 to 750,000 weight-average molecular weight. Representative of polyalkylene oxides are polyethylene oxide of 100,000 weight-average molecular weight, polyethylene oxide of 200,000 weight-average molecular weight, polyethylene oxide of 300,000 weight-average molecular weight, polyethylene oxide of 600,000 weight-average molecular weight, and polypropylene oxide of 100,000 weight average molecular weight. The therapeutic composition may also comprise 0 mg to 50 mg, in a present manufacture 1 mg to 50 mg of a hydroxypropylalkylcellulose of 9,000 to 150,000 average-number molecular weight selected from the group consisting of hydroxypropylmethylcellulose, hydroxypropylethylcellulose, hydroxypropylbutylcellulose, and hydroxypropylpentylcellulose, 0 to 20 mg of a hydroxyalkylcellulose, such as hydroxypropylcellulose; 0 mg to 50 mg, in a present manufacture 1 mg to 50 mg, of an osmotic solute selected from the osmotically effective compounds consisting of sodium chloride, potassium chloride, potassium acid phosphate, tartaric acid, citric acid, raffinose, magnesium sulfate, magnesium chloride, urea, inositol, sucrose, glucose and sorbitol; and 0.00 mg to 7.5 mg and one manufacture 0.01 mg to 5 mg of a lubricant, such as calcium stearate, zinc stearate, magnesium stearate, magnesium oleate, calcium palmitate, sodium suberate, potassium laureate, salts of fatty acids, salts of alicyclic acids, salts of aromatic acids, stearic acid, oleic acid, palmitic acid, and a mixture of salt of fatty, alicyclic or aromatic acid and a fatty, alicyclic or aromatic acid.

The invention provides for the therapeutic composition comprising the drug oxybutynin to be administered as the composition neat, that is, oxybutynin alone, for increasing the urinary bladder capacity, for diminishing the frequency of uninhibited contractions of the detrusor muscles and its accompanying delay of the desire to void. The invention provides for the therapeutic oxybutynin composition to be surrounded by a wall comprising a semipermeable composition with an exit for delivering the therapeutic composition to a human patient in need of oxybutynin therapy. The invention provides, in an additional embodiment, the therapeutic composition comprising oxybutynin as a therapeutic layer in layered, contacting arrangement with a hydrogel expansion composition manufactured as a layer that supports the therapeutic composition to yield a bilayered matrix. The hydrogel layer composition may comprise 10 mg to 350 mg of a hydrogel, such as a member selected from the group consisting of a polyalkylene oxide of 1,000,000 to 8,000,000 which are selected from the group consisting of polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight, and a polypropylene oxide of the 1,000,000 to 8,000,000 weight-average molecular weights; or 10 mg to 250 mg of an alkali carboxymethylcellulose of 10,000 to 6,000,000 weight-average molecular weight such as sodium carboxymethylcellulose or potassium carboxymethylcellulose. The hydrogel expansion layered comprises 0.0 mg to 350 mg, in present manufacture 0.1 mg to 250 mg of a hydroxyalkylcellulose of 7,500 to 4,500,000 weight-average molecular weight, represented by hydroxymethylcellulose, hydroxyethylcellulose, hydroxypropylcellulose, hydroxybutylcellulose, and hydroxypentylcellulose; 0 mg to 50 mg, in present manufacture 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

The invention provides for the therapeutic oxybutynin composition, the therapeutic bilayer comprising the drug oxybutynin layer, and the osmopolymer hydrogel layer to be administered as the composition or the bilayer per se; that is, as the composition or the bilayer together for increasing the urinary bladder capacity, for diminishing the frequency of uninhibited contractions of the detrusor muscles and its accompaying delay of the desire to void. The invention provides additionally for the therapeutic composition and for the compositional bilayer to be surrounded by a wall comprising a semipermeable composition with an exit for delivering the therapeutic composition to a human patient in need of oxybutynin therapy. The invention also provides for a subcoat to surround the therapeutic composition or to surround the bilayer, which subcoat in either embodiment is surrounded by a outer semipermeable wall.

The invention provides a dosage form for the delivery of the therapeutic composition comprising oxybutynin. The dosage form comprises up to 650 mg, and provides a sustained release at a controlled rate up to 25 mg, of oxybutynin or its salt up to 24 hours. The dosage form comprises a wall, which wall surrounds an internal lumen or compartment. The wall comprises a semipermeable composition that is permeable to the passage of fluid and impermeable to the passage of oxybutynin. The wall is nontoxic and it comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or hydroxypropylalkycellulose such as hydroxypropylmethylcellulose. The total weight percent of all components comprising the wall is equal to 100 wt %. The internal compartment comprises the therapeutic oxybutynin composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of oxybutynin to a patient over time. The dosage form comprises a passageway in the wall that connects the exterior of the dosage form with the internal compartment. The osmotic powered dosage form provided by the invention delivers oxybutynin from the dosage form to the patient at a zero order rate of release over a period of 24 hours.

The expression "passageway" as used herein comprises means and methods suitable for the metered release of the therapeutic drug from the compartment of the dosage form. The exit means comprises at least one passageway, including orifice, bore, aperture, pore, porous element, hollow fiber, capillary tube, channel, porous overlay, or porous element that provides for the osmotic controlled release of oxybutynin. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leachable polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of oxybutynin from the dosage form. The dosage form can be constructed with one or more passageways in spaced apart relationship on a single surface or on more than one surface of the wall. The expression "fluid environment" denotes an aqueous or biological fluid as in a human patient, including the gastrointestional tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

DESCRIPTION FOR MANUFACTURING THE COMPOSITIONS AND DOSAGE FORMS OF THE INVENTION

The wall of dosage forms can be formed by using an air suspension procedure. This procedure consists of suspending and tumbling the composition or the layers in a current of air and wall-forming composition until a wall is applied to the oxybutynin forming compartment. The air suspension procedure is well suited for independently forming the wall. The air suspension procedure is described in U.S. Patent No. 2,799,241; *J. Am. Pharm. Assoc.*, Vol. 48, pp. 451–454 (1959); and ibid, Vol. 49, pp. 82–84 (1960). The wall can be formed with a wall-forming composition in a Wurster® air suspension coater using an organic solvent, such as acetone-water cosolvent 90:10 (wt:wt) with 2.5 wt % to 7 wt % polymer solids. An Aeromatic® air suspension coater using, for example, a methylene dichloride-methanol cosolvent comprising 87:13 (v:v) can be used for applying the wall. Other wall-forming techniques, such as pan coating system, wall forming compositions deposited by successive spraying of the composition or the bilayered arrangement, accompanied by tumbling in a rotating pan can be used for the present purpose. A larger volume of cosolvent can be used to reduce the concentration of polymer solids to produce a thinner wall. Finally, the wall of the coated compartments are laser or mechanically drilled, and then dried in a forced air or humidity oven for 1 to 3 days or longer to free the solvent. Generally, the walls formed by these techniques have a thickness of 2 to 20 mils (0.051 to 0.510 mm) with a preferred thickness of 2 to 6 mils (0.051 to 0.150 mm).

The dosage forms of the invention are manufactured by standard manufacturing techniques. For example, in one manufacture the beneficial drug oxybutynin and/or additional drugs such as an estrogen, a steroid pair such as an estrogen and a progestin, and other ingredients comprising a therapeutic composition or comprising the drug composition that faces the exit means are blended, or they are blended then pressed into a composition. The oxybutynin and other ingredients can be blended with a solvent and then formed into a solid or semisolid formed by conventional manufacturing methods such as ball-milling, calendaring, sitrring, or roll-milling and then pressed into a selected shape. The composition possesses dimensions that correspond to the internal dimensions of the area it occupies in the dosage form. In the manufacture of bilayered compositions dosage form, the bilayers posses dimensions corresponding to the internal lumen of the dosage form. First, the hydrogel expansion layer is placed in contact with the oxybutynin layer. The layering of the oxybutynin layer and the hydrogel layer can be fabricated by conventional press-layering techniques. Finally, the two-layer compartment forming members are surrounded and coated with an outer wall. A passageway is drilled by laser or mechanically drilled through the wall, or the wall is provided with a pore-former to contact the oxybutynin layer, with the dosage form optically oriented automatically by the equipment for laser forming the passageway on the preselected drug surface.

In another manufacture, the dosage forms are manufactured by the wet granulation technique. In the wet granulation technique the oxybutynin and/or other drugs, and the ingredients comprising the drug composition are blended using an organic or inorganic solvent, such as isopropyl alcohol-methylene dichloride 80:20 (v:v) as the granulation fluid. Other granulating fluid, such as water, isopropyl alcohol, or denatured alcohol 100% can be used for this purpose. The ingredients forming the drug composition are individually passed through a 40 mesh screen and then thoroughly blended in a mixer. Next, other ingredients comprising the drug composition are dissolved in a portion of the granulation fluid, such as the cosolvent described above. Then, the latter prepared wet blend is slowly added to the drug oxybutynin blend with continual mixing in the blender. The granulating fluid is added until a wet blend mass is produced, which wet mass is then forced through a 20 mesh screen onto oven trays. The blend is dried for 18 to 24 hours at 25° C. to 40° C. The dry granules are then screened with a 16 mesh screen. Next, a lubricant is passed through an 60 mesh screen and added to the dry screened granule blend. The granulation is put into milling jars and mixed on a jar mill for 2 to 10 minutes. The first and second layer compositions are pressed into a layered tablet, for example, in a Manesty® layer press.

Another manufacturing process that can be used for providing a oxybutynin and hydrogel composition comprises blending their powdered ingredients in a fluid bed granulator. After the powdered ingredients are dry blended in the granulator, a granulating fluid, for example, poly (vinylpyrrolidone) in a solvent, such as in water, is sprayed onto the respective powders. The coated powders are then dried in a granulator. This process coats the ingredients present therein while spraying the granulating fluid. After the granules are dried, a lubricant, such as stearic acid or magnesium stearate, is blended as above into the mixture. The granules are then pressed in the manner described above. In another embodiment, when the fluid bed granulating process is used to manufacture the hydrogel layer, the antioxidant present in the polyalkylene oxide can be removed during the processing step. If antioxidant is desired it can be added to the hydrogel formulation, and this can be accomplished during the fluid bed granulation process.

The dosage forms of this invention are manufactured in another embodiment by mixing the oxybutynin with composition-forming ingredients and pressing the composition into a layer possessing dimensions that correspond to the internal dimensions of the compartment space adjacent to a passageway. In another embodiment, the oxybutynin and other drug composition forming ingredients and a solvent are mixed into a solid, or semi-solid, by conventional methods such as ball-milling, calendaring, stirring or roll-milling, and then pressed into a preselected, layer-forming shape. The invention provides further a method of manufacturing a sustained release dosage form adapted for managing oxybutynin and its desethylmetabolite in plasma by incorporating an effective amount of oxybutynin or its salt in a controlled release dosage form that releases oxybutynin continuously at a controlled rate to provide a higher oxybutynin concentration and a lower desethylmetabolite concentration than provided by an immediate release dosage form that dose-dumps. An immediate release dosage form generally dose-dumps its drug in an hour or less, as it lack prolonged delivery.

In the manufactures as presented above, the manufacture comprising a composition or comprising a layer of a composition comprising a hydrogel osmopolymer and an optional osmagent are placed in contact with the layer comprising the drug oxybutynin, and the two layers comprising the layers are surrounded with a semipermeable wall. The layering of the first drug oxybutynin composition and the second hydrogel osmopolymer and optional osmagent composition can be accomplished by using a conventional two-layer tablet press technique. The wall can be applied by molding, spraying or dipping the pressed shapes into wall-forming materials. Another technique that can be used for applying the wall is the air suspension coating procedure. This procedure consists in suspending and tumbling the two layers in a current of air until the wall forming composition surrounds the layers. Manufacturing procedures are described in *Modern Plastics Encyclopedia*, Vol. 46, pp. 62–70 (1969); and in *Pharmaceutical Sciences*, by Remington, 14$^{th}$ Ed., pp. 1626–1680 (1970), published by Mack Publishing Co., Easton, Pa. The dosage form can be manufactured by following the teaching in U.S. Pat. Nos. 4,327,725; 4,612,008; 4,783,337; 4,863,456; and 4,902,514.

The dissolution of a drug indicates the drug entering into solution upon its delivery from a dosage form provided by this invention is measured by the following procedure. First, a drug receiving solution, such as, gastrointestinal fluid, hydrochloric acid, or an aqueous sodium dodecyl sulfate, 1% (w/v) (weight/volume) solution is used as the dissolution media. A dosage form prepared by this invention is placed into the dissolution media and the drug released by the dosage form into the dissolution media is sampled at a constant time interval over the time period of dissolution. The filtered samples are assayed by a reversed high pressure liquid chromatography, or detection by UV. The concentration of the samples is measured against a standard curve containing, for example, at least five standard points. Procedures for dissolution testing are reported in *The United States Pharmacopoeia*, The National Formulary, pp. 1791 to 1796; (1995); *Pharmaceutical Sciences*, by Remington, 17$^{th}$ Ed., pp. 653–666 (1985); and *USP XXII*, Dissolution Paddle Analysis, pp. 1578–1579 (1990).

The release rate of drug from a dosage form manufactured by this invention can be ascertained by the following procedure. The procedure comprises placing the dosage form in a solution, usually water, and taking aliquots of the release rate solution, followed by their injection into a chromatographic system to quantify the amount of drug released during specified test intervals. The drug, for example, is resolved on a column and detected by UV absorption. Quantitation is performed by linear regression analysis of peak areas from a standard curve containing at least five standard points.

The release rate procedure comprises attaching a dosage form to a plastic rod with the orifice exposed to the drug receiving solution. Then, attaching the rod to a release arm, with the arm affixed to an up/down reciprocating shaker, which operates at an amplitude of about 3 cm and 2 seconds per cycle. Then, continuously immersing the dosage form in 50 ml test tubes containing 30 ml of $H_2O$, equilibrated in a constant temperature water bath at 37° C.±0.5° C. Next, at the end of each interval, transfer the dosage form to the next row of new test tubes containing a receiving solution, such as water. After the release pattern is complete, remove the tubes and allow to cool to room temperature, followed by filling the calibrated tubes to the 50 ml mark with a solvent, such as acetone. The samples are mixed immediately, transferred to sample vials, followed by chromatography analysis.

Exemplary solvents suitable for manufacturing the wall, the composition layers and the dosage form include inert inorganic and organic solvents that do not adversely harm the materials, the wall, the layer, the composition and the drug wall. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethylacetate, methylene dichloride, ethylene dichloride, propylene dichloride, carbon chloroform, nitroethane, nitropropane, tetrachloroethane, ethyl ether, isopropyl ether, cyclohexane, cyclo-octane, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DISCLOSURE OF EXAMPLES PROVIDED BY THE INVENTION

The following examples are merely illustrative of the present invention and they should not be considered as limiting the scope of the invention in any way. These examples and other equivalents thereof will become apparent to those versed in the art in the light of the present disclosure and the accompanying claims.

Example 1

A therapeutic oxybutynin composition for administering to a patient and for use in the invention was prepared as follows: First, 103 grams of oxybutynin hydrochloride was dissolved in 1200 ml (milliliters) of anhydrous ethanol. Separately, 2,280 g of polyethylene oxide of 200,000 weight-average molecular weight, 150 g of hydroxypropylmethylcellulose of 9,200 average-number molecular weight and 450 g of sodium chloride were dry blended in a conventional blender for 10 minutes to yield a homogenous blend. Next, the oxybutynin ethanol solution was added slowly to the blend, with the blender continuously blending until all the ingredients were added to the three component dry blend, with the blending continued for another 8 to 10 minutes. The blended wet composition was passed through a 16 mesh screen and dried overnight at a room temperature of 72° F. (22.2°). Then, the dry granules were passed through a 20 mesh screen, 18 g of magnesium stearate was added, and all the ingredients blended again for 5 minutes. The fresh granules are ready for formulation into a therapeutic oxybutynin composition. The therapeutic composition comprises 3.4 wt % oxybutynin hydrochloride, 76 wt % polyethylene oxide of 200,000 weight-average molecular weight, 5 wt % of hydroxypropylmethylcellulose of 9,200 average-number molecular weight, 15 wt % sodium chloride, and 0.6 wt % magnesium stearate. The therapeutic composition can be administered for its intended oxybutynin therapy, the management of overactive bladder.

Example 2

An osmopolymer hydrogel composition for use in the invention was prepared as follows: first 1274 g of pharmaceutically acceptable polyethylene oxide comprising a 7,500,000 weight-average molecular weight, 600 g of sodium chloride, and 20 g of colorant ferric oxide were separately screened through a 40 mesh screen. Then, all the screened ingredients were mixed with 100 g of hydroxypropylmethylcellulose of 11,200 average-number molecular weight to produce a homogenous blend. Next, 300 ml of denatured anhydrous alcohol was added slowly to the blend with continuous mixing for 5 minutes. Then, 1.6 g of butylated hydroxytoluene was added, followed by more blending, with 5 g of magnesium stearate added with 5 minutes of blending, to yield a homogenous blend. The freshly prepared granulation is passed through a 20 mesh screen and allowed to dry for 20 hours at 22.2° C. The final composition comprised 63.67 wt % polyethylene oxide of 7,500,000 weight-average molecular weight, 30 wt % sodium chloride, 1 wt % ferric oxide, 5 mg hydroxypropylmethylcellulose of 11,200 average-number molecular weight, 0.08 wt % butylated hydroxytoluene, and 0.25 mg magnesium stearate.

Example 3

An osmopolymer hydrogel composition for use in the invention was prepared as follows: first 1274 g of pharmaceutically acceptable sodium carboxymethylcellulose comprising a 2,250,000 weight-average molecular weight, 600 g of sodium chloride, and 20 g ferric oxide were separately screened through a 40 mesh screen. Then, all the screened ingredients were mixed with 100 g of hydroxypropylmethylcellulose of 11,200 average-number molecular weight and 100 g of hydroxypropylcellulose of 30,000 average-number molecular weight to produce a homogenous blend. Next, 300 ml of denatured anhydrous alcohol was added slowly to the blend with continuous mixing for 5 minutes. Then, 1.6 g of butylated hydroxytoluene was added, followed by more blending, with 5 g of magnesium stearate added with 5 minutes of blending, to yield a homogenous blend. The freshly prepared granulation was passed through a 20 mesh screen and allowed to dry for 20 hours at 22.2° C. The final composition comprised 68.67 wt % the sodium carboxymethylcellulose, 30 wt % sodium chloride, 1 wt % ferric oxide, 5 mg of hydroxypropylmethylcellulose, 5 mg hydroxypropylcellulose, 0.08 wt % butylated hydroxytoluene, and 0.25 mg of magnesium stearate.

Example 4

The therapeutic oxybutynin composition and the osmopolymer hydrogel composition were made into a bilayered tablet as follows: first, 147 mg of the oxybutynin composition as prepared in Example 1 was added to a punch die set and tamped. Then, 98 mg of the hydrogel composition as prepared in Example 2 was added and the two layers compressed under a pressure head of 1.0 ton (1000 kg) into a $^{11}/_{32}$ inch (0.873 cm) diameter, contacting intimate bilayered tablet. The example was repeated with the hydrogel composition as prepared in Example 3 to produce the tablet comprising two layers.

Example 5

The bilayered tablet for example as described in Example 4 was manufactured into a dosage form as follows: first, a semipermeable wall-forming composition was prepared comprising 95 wt % cellulose acetate having a 39.8% acetyl content, and 5 wt % polyethylene glycol having a number-average molecular weight of 3350 by dissolving the ingredients in a cosolvent comprising acetone and water in 90:10 wt:wt composition to make a 4% solid solution. The wall-forming composition was sprayed onto and around the bilayered cores as prepared in Examples 2 and 3 to provide a 26.4 mg semipermeable wall.

Next, the semipermeable walled, bilayered tablet was laser drilled to provide a 20 mil (0.51 mm) orifice to contact the oxybutynin layer and the exterior of the dosage form. The residual solvent was removed by drying for 48 hours at 50° C. and 50% relative humidity. Next, the dosage forms were dried further for 1 hour at 50° C. to remove excess moisture. The dosage form provided by this manufacture provides 3.4 wt % oxybutynin hydrochloride, 76 wt % polyethylene oxide of 200,000 weight-average molecular weight, 5 wt % hydroxypropylmethylcellulose of 9,200 average-number molecular weight, 0.6 wt % magnesium stearate, and 15 wt % sodium chloride in the therapeutic oxybutynin composition. The osmopolymer hydrogel push composition comprises 63.67 wt % polyethylene oxide of 7,500,000 weight-average molecular weight, 30 wt % sodium chloride, 1 wt % ferric chloride, 5 wt % hydroxypropylmethylcellulose of 9,200 average-number molecular weight, 0.08 wt % butylated hydroxytoluene, and 0.25 wt % magnesium stearate. The semipermeable wall comprises 95 wt % cellulose acetate comprising 39.8% acetyl content, and 5 wt % polyethylene glycol of 3350 number-average molecular weight. The dosage form comprises an exit passage of 20 mils (0.50 mm) and it has a mean release rate of 0.260 mg/hr for 23.8 hours. The semipermeable wall provides substantial protection from photo (light) degradation of the oxybutynin in the dosage form.

Example 6

A dosage form is prepared according to the above examples, comprising a drug layer comprising of 6.67 wt % oxybutynin hydrochloride, 87.83 wt % polyethylene oxide of 200,000 weight-average molecular weight, 4.00 wt % hydroxypropylmethylcellulose of 9,200 average-number molecular weight, and 0.50 wt % magnesium stearate; in layered contact with a push hydrogel layer comprising 58.75 wt % sodium carboxymethylcellulose of 6,000,000 weight-average molecular weight, 30 wt % sodium chloride, 5.00 wt % hydroxypropylmethylcellulose of 9,200 average-number molecular weight, 1.00 wt % ferric oxide, 5.00 wt % hydroxypropylcellulose of 75,000 average-number molecular weight and 0.25 wt % magnesium stearate; which bilayered core is surrounded by a semipermeable wall comprising cellulose acetate and polyethylene glycol; and an exit port through the wall for delivering the oxybutynin at a controlled rate over thirty hours.

Example 7

The dosage form according to Example 6 wherein in the drug composition the polyethylene oxide has a 300,000 weight-average molecular weight; the hydroxypropylcellulose is a member selected from the group consisting of 25,000, 30,000, or 40,000 average-number molecular weight; and the dosage form comprises 5 mg to 250 mg of oxybutynin pharmaceutically acceptable salt.

Example 8

A dosage form was prepared according to the above examples wherein the dosage form of this example comprises a drug oxybutynin layer comprising 5 mg oxybutynin, 111.60 mg polyethylene oxide of 200,000 weight-average molecular weight, 7.35 mg hydroxypropylmethylcellulose of 9,200 average-number molecular weight, 0.88 mg magnesium stearate, 22.05 mg of sodium chloride, and 0.12 mg of butylated hydroxytoluene; a hydrogel push layer comprising 62.40 mg of polyethylene oxide of 7,000,000 weight-average molecular weight, 29.40 mg of sodium chloride, 4.90 mg hydroxypropylmethylcellulose of 9,200 average-number molecular weight, 0.08 mg of butylated hydroxytoluene, 0.98 mg of red ferric oxide, and 0.24 mg of magnesium stearate; a wall comprising cellulose acetate consisting of a 39.8% acetyl content and polyethylene glycol of 3350 number-average molecular weight in the percentage ratio of 95 wt % cellulose acetate to 5 wt % polyethylene glycol, and exit means in the wall.

Example 9

A dosage form was prepared according to the examples provided by this invention wherein the dosage form comprises: a drug anticholinergic oxybutynin layer comprising 5.3 wt % oxybutynin, 82.37.wt % polyethylene oxide of 200,000 weight-average molecular weight, 2 wt % hydroxypropylmethylcellulose of 9,200 average-number molecular weight, 0.25 wt % magnesium stearate, 10 wt % sodium chloride, and 0.08 wt % butylated hydroxytoluene; a push hydrogel layer comprising 63.37 wt % polyethylene oxide of 2,000,000 weight-average molecular weight, 30 wt % sodium chloride, 5 wt % hydroxypropylmethylcellulose of 9,200 average-number molecular weight, 0.08 wt % butylated hydroxytoluene, 1 wt % black ferric oxide and 0.25 wt % magnesium stearate; a wall comprising 99 wt % cellulose acetate comprising a 39.8% acetyl content and 1 wt % polyethylene glycol of 3350 number-average molecular weight; and an exit passageway through the wall for delivering the oxybutynin to a patient, for treatment of symptoms in neurogenic bladder.

Example 10

An oxybutynin composition was prepared according to the above examples, wherein the composition comprises 10.6% oxybutynin hydrochloride, 79.57 wt % polyethylene oxide of 200,000 weight-average molecular weight, 2 wt % hydroxypropylmethylcellulose of 9,200 average-number molecular weight, 0.25 wt % of magnesium stearate, 7.5 wt % of sodium chloride, and 0.08 wt % butylated hydroxytoluene.

Example 11

An oxybutynin composition was prepared according to the above examples wherein the composition comprises 16 wt % oxybutynin hydrochloride, 76.67 wt % polyethylene oxide of 200,000 weight-average molecular weight, 2 wt % hydroxypropylmethylcelluose of 9,200 average-number molecular weight, 0.25% magnesium stearate, 5 wt % sodium chloride, and 0.08 wt % butylated hydroxytoluene.

Example 12

A hydrogel composition was prepared according to the above examples wherein the composition comprises 58.75 wt % hydroxyethylcellulose of 1,300,000 weight-average molecular weight, 30 wt % sodium chloride, 10 wt % polyvinylpyrrolidone of 42,000 viscosity-average molecular weight, 1 wt % colorant red ferric oxide, and 0.25 wt % magnesium stearate.

Example 13

A dosage form was prepared according to the present invention wherein the dosage form comprises: a drug layer comprising 3.4 wt % oxybutynin hydrochloride, 76 wt % polyethylene oxide of 200,000 weight-average molecular weight, 5 wt % hydroxypropylmethylcellulose of 9,200 average-number molecular weight, 0.6 wt % magnesium stearate, 15 wt % sodium chloride, a push hydrogel layer comprising 58.75 wt % hydroxyethylcellulose of 1,300,000 average-number molecular weight, 30 wt % sodium chloride, 10 wt % polyvinylpyrrolidone of 42,000 viscosity-average molecular weight, 1 wt % red ferric oxide, and 0.25 wt % magnesium stearate; a wall comprising 95 wt % cellulose acetate comprising a 39.8% acetyl content, and 5 wt % polyethylene glycol of 3350 number-average molecular weight, an exit orifice of 20 mil (0.50 mm); and a release rate of 0.292 mg per 1 hour for 16.9 hours.

Example 14

A dosage form was manufactured according to the present examples wherein the dosage form comprises: a drug oxybutynin composition comprising 3.4 wt % oxybutynin hydrochloride, 76 wt % polyethylene oxide of 200,000 weight-average molecular weight, 5 wt % hydroxypropylmethylcellulose of 9,200 average-number molecular weight, 0.6 wt % of magnesium stearate, and 15 wt % sodium chloride; a push hydrogel composition for pushing the drug oxybutynin composition form the dosage form comprising 63.67 wt % polyethylene oxide of 7,000,000 weight-average molecular weight, 30 wt % sodium chloride, 1 wt % red ferric oxide, 5 wt % hydroxypropylmethylcellulose of 9,200 average-number molecular weight, 0.08 wt % butylated hydroxytoluene, and 0.25 wt % magnesium stearate; a subcoat that surrounds the drug oxybutynin composition and push hydrogel composition wherein the subcoat comprises 95 wt % hydroxyethylcellulose, a nonionic water soluble polymer of 90,000 average-number molecular weight; then an outer wall or overcoat comprising 95 wt % cellulose acetate possessing an acetyl content of 39.8% and 5 wt % polyethylene glycol of 3,350 number-average molecular weight; a 20 mil (0.50 mm) exit passageway; and an oxybutynin release rate of 0.295 mg per 1 hour over 19.9 hours.

Example 15

A dosage form designed and shaped as a pharmaceutically acceptable tablet for the oral administration of a member selected from the group consisting of oxybutynin and its pharmaceutically acceptable salts was made by following the above examples. The dosage form provided by the example comprises a drug composition weighing 92 mg comprising 5.45 wt % of oxybutynin hydrochloride, 9.98 wt % of sodium chloride, 82.16 wt % of polyethylene oxide of 100,000 of weight-average molecular weight, 2.00 wt % of hydroxypropylmethylcellulose of 11,300 of average-number molecular weight, 0.25 wt % of magnesium stearate, 0.08 wt % of butylated hydroxytoluene, and 0.05 wt % of green ferric oxide. The composition was surrounded by a wall comprising a semipermeable cellulose acetate polymer comprising a 39.8% acetyl content and polyethylene glycol comprising a 3,350 molecular weight. The dosage form comprised an exit in communication with the oxybutynin composition for delivering oxybutynin to the gastrointestinal tract of a patient.

Example 16

A dosage form adapted as an orally administrable caplet was made according to the above examples. The dosage form of this example comprises a drug composition weighing 92 mg and comprising 5.45 wt % oxybutynin hydrochloride, 9.98 wt % sodium chloride, 82.19 wt % polyethylene oxide possessing a 200,000 weight-average molecular weight, 2.00 wt % hydroxypropylmethylcellulose of 11,300 molecular weight, 0.25 wt % magnesium stearate, 0.08 wt % butylated hydroxytoluene, and 0.05 wt % colorant green ferric oxide; a push composition initially in contact with the drug composition, weighing 62 mg and comprising 63.67 wt % polyethylene oxide possessing a 2,000,000 weight-average molecular weight, 30.00 wt % sodium chloride, 5.00 wt % hydroxypropylmethylcellulose of 11,200 molecular weight, 1.00 wt % of a 95.5 mixture of colorant black iron oxide/lactose, 0.25 wt % magnesium stearate, and 0.08 wt % butylated hydroxytoluene; a wall weighing 19 mg that surrounds the compositions and comprises 99 wt % of cellulose acetate of 39.8% acetyl content, and 1.00 wt % polyethylene glycol of 3,350 molecular weight; a yellow color overcoat weighing 10 mg; and an exit in the wall for delivering the drug to a patient. The dosage form exhibited a cumulative release of oxybutynin hydrochloride of greater than zero mg to 1 mg in 0 to 4 hours, 1 mg to 2.5 mg in 0 to 8 hours, 2.75 mg to 4.25 mg in 0 to 14 hours, and 3.75 mg to 5 mg in 0 to 24 hours.

Example 17

A dosage form for the oral administration of oxybutynin was made by following the above examples. The dosage form comprises a 92 mg drug composition comprising 10.90 wt % oxybutynin hydrochloride, 7.48 wt % sodium chloride, 79.25 wt % polyethylene oxide possessing a 200,000 weight-average molecular weight, 1.99 wt % hydroxypropylmethylcellulose possessing a 11,300 molecular weight, 0.25 wt % magnesium stearate, 0.08 wt % butylated hydroxytoluene, and 0.25 wt % magnesium stearate, 0.08 wt % butylated hydroxytoluene, and 0.05 wt % colorant red ferric oxide; a push composition weighing 62 mg and comprising 63.67 wt % polyethylene oxide possessing a 2,000,000 weight-average molecular weight, 30 wt % sodium chloride, 5 wt % hydroxypropylmethylcellulose possessing a 11,300 molecular weight, 1.00 wt % colorant black iron oxide/lactose (95:5), 0.25 wt % magnesium stearate, and 0.08 wt % butylated hydroxytoluene; a semipermeable wall that envelopes the compositions weighting 19 mg comprising 99 wt % cellulose acetate comprising a 39.8 acetyl content, and 1 wt % polyethylene glycol 3350; a exit in the wall; and a 10 mg color overcoat. The dosage form, when in operation operates by osmotic kinetics, and delivers in 0 to 4 hours up to 20% (up to 2 mg) of oxybutynin hydrochloride, in 0 to 8 hours 20 to 50% (2.0 to 5.0 mg) of oxybutynin salt; in 0 to 14 hours 50 to 85% (5.5 mg to 8.5 mg) of oxybutynin; and 0 to 24 hours greater than 75% (greater than 7.5 mg) of the drug. The dosage form can be manufactured shaped like a pharmaceutically acceptable tablet, or the dosage form can be manufactured shaped like a pharmaceutically acceptable capsule.

Example 18

A dosage form for the oral delivery of a member selected from the group consisting of oxybutynin and its pharmaceutically acceptable salts was made according to the above examples. The dosage form comprised a drug composition weighing 92 mg comprising 16.30 wt % oxybutynin chloride, 4.98 wt % sodium chloride, 76.35 wt % polyethylene oxide of 200,000 molecular weight, 1.99 wt % hydroxypropylmethylcellulose, 0.25 wt % magnesium stearate, 0.08 wt % butylated hydroxytoluene, 0.02 wt % black iron oxide/lactose (95:5); a push composition weighing 62 mg comprising 63.67 wt % polyethylene oxide possessing a 2,000,000 molecular weight, 30.00 wt % sodium chloride, 5.00 hydroxypropylmethylcellulose of 11,300 molecular weight, 1.00 wt % black iron oxide/lactose (95:5), 0.25 wt % magnesium stearate, and 0.08 wt % butylated hydroxytoluene; a wall weighing 19 mg comprising a semipermeable composition permeable to a fluid flux, impermeable to drug flux comprising 99.00 wt % cellulose acetate having a 39.8 acetyl content, and 1.00 wt % polyethylene glycol 3350; a passageway in the wall; and a overcoat weighing 10 mg colored grey. The dosage form exhibited a cumulative release rate of up to 3 mg in 0 to 4 hours; 3 mg to 7.5 mg in 0 to 8 hours; 8 mg to 13 mg in 0 to 14 hours; and 12 mg to 15 mg in 0 to 24 hours.

Example 19

A dosage form was prepared according to the previous examples comprising an oxybutynin salt, that delivers up to 1.60 mg in 0 to 4 hours, up to 5 mg in 0 to 8 hours, up to 8.5 mg in 0 to 12 hours, up to 11 mg in 0 to 16 hours, and up to 15 mg in 0 to 24 hours.

Example 20

An orally administrable dosage form comprising 1 mg to 100 mg of a drug selected from the group consisting of oxybutynin and its pharmaceutically acceptable salt is prepared by following the previous examples, for administering accompanied by a different drug, or prior to or after the administration of conjugated equine estrogens.

Example 21

A dosage form is prepared according to the above examples wherein the dosage form of this example comprises a drug oxybutynin steroid composition comprising 5 mg oxybutynin, 0.3 mg conjugated estrogens, 111.60 mg polyethylene oxide of 200,000 weight-average molecular weight, 7.35 mg hydroxypropylmethylcellulose of 9,200 average-number molecular weight, 0.88 mg magnesium stearate, 22.05 mg of sodium chloride, and 0.12 mg of butylated hydroxytoluene; a hydrogel push composition comprising 62.40 mg of polyethylene oxide of 7,000,000 weight-average molecular weight, 29.40 mg of sodium chloride, 4.90 mg hydroxypropylmethylcellulose of 9,200 average-number molecular weight, 0.08 mg of butylated hydroxytoluene, 0.98 mg of red ferric oxide, and 0.24 mg of magnesium stearate; a wall comprising cellulose acetate consisting of a 39.8% acetyl content and polyethylene glycol of 3350 number-average molecular weight in the percentage ratio of 95 wt % cellulose acetate to 5 wt % polyethylene glycol, and an exit passageway in the wall.

Example 22

A dosage form is prepared according to the previous example, wherein the dosage form comprises a drug composition comprising oxybutynin in a dose of 5 mg to 20 mg of oxybutynin and at least one of a steroid member selected from the dose group consisting of 0.3 mg, 0.625 mg, 0.9 mg, 1.25 mg and 2.5 mg of a mixture of estrogen sulfates, estrone, equilin, 17α-dihydroequilin, 17α-estradiol, equilenin and 17α-dihydroequilenin indicated for treating urge incontinence, the symptoms associated with menopause, and hormone replacement therapy.

Example 23

A bioerodible dosage form is prepared comprising a bioerodible polymer in matrix dosage form comprising 5 mg of oxybutynin and 0.3 mg of an estrogen that provides for the drugs release at controlled rate by the bioeroding matrix over 24 hours. The bioerodible polymer forming the dosage form matrix comprises a member selected from the group consisting of poly(ester), poly(amine), poly(lactide), poly (glycolide), poly(lactide-co-glycolide), poly(caprolactone), poly(hydroxybutynin acid), poly(orthoester), poly (orthocarbonate), poly(dihydropyran), poly(3-hydroxybutyrate-co-3-hydroxyvalerate), and poly(3-hydroxybutyrate-co-hydroxybutyrate). An additional dosage form can be prepared according to the example that administers a member selected from oxybutynin and its pharmaceutically acceptable salt and 30 μg ethinyl estradiol and 150 μg of levonorgestrel.

Example 24

A diffusion rate-controlled dosage form that comprises a diffusion-rate controlled polymer through which oxybutynin and a steroid is released by diffusion is prepared by formulating oxybutynin and a member selected from the group consisting of a progestin and estrogen pair, and an estrogen, in a polymer matrix. The diffusion can be through the polymer or through a porous-polymer membrane. The diffusion dosage form structurally includes a polymer matrix that is a reservoir for the drug(s), or through a contacting polymer rate-governing membrane. Representative of polymers for providing diffusional dosage forms comprise a member selected from the group consisting of poly(olefin), poly(vinyl), poly(carbohydrate), poly(peptide), poly (condensation), poly(rubber), and poly(silicon). Representative of specific polymers consists of a member selected from the group consisting of poly(ethylene), poly (propylene), copoly(ethylene-vinyl acetate), poly (isobutylethylene), poly(vinylaurate), cross-linked poly (vinylalcohol), poly(methacrylate), poly(amide), poly (ester), and poly(silicone).

Example 25

A dosage form comprising ion-exchange activity is prepared and it comprises a water-insoluble crosslinked polymer with oxybutynin and estrogen bound to the ion-exchange resin. The drugs are released at a rate controlled by the drug-resin complex by the ionic environment within the gastrointestinal tract. The ion-exchange resins that can be adapted for the manufacture of the dosage form comprise a cation-exchange resin and an anion-exchange resin. The cation-exchange resins include strong-acid and weak-acid resins as with sulfonic acid, carboxylic acid, and phosphonic acid and the anion-exchange resins include strong-base and weak-base resins as with quaternary ammonium, secondary amine, tertiary amine aromatic and tertiary amine aliphatic resins. Specific examples of ion-exchange resins such as Amberlite IR-120, basic ion-exchange resins such as Amberlite IRA-400, and weak basic ion-exchange resins such as Amberlite IR-45.

Example 26

A method of manufacturing a sustained release dosage form for managing the concentration of oxybutynin and its desethylmetabolite in plasma, is provided, which method of manufacture comprises the incorporation of an effective amount of oxybutynin or its pharmaceutically acceptable salt in a sustained and controlled release dosage form which release oxybutynin continuously at a controlled zero order rate to provide a relatively higher oxybutynin concentration and a relatively lower desethylmetabolite concentration than provided by an immediate release non-sustained dosage form profile.

METHOD OF PRACTICING THE INVENTION

The drug oxybutynin, identified as OXY, was administered in a clinical study to a number of patients to treat urinary incontinence. Patients who self-administered oxybutynin often quit or discontinue treatment due to its anticholinergic side effects, which appear to be peak-concentration related. The present invention thus provides a sustained release (SR) controlled-release (CR) oral dosage form comprising oxybutynin designed to provide both oxybutynin therapy through the entire gastrointestional tract and a continuous plasma drug concentration that avoid peak and valley concentrations. The sustained release dosage form of this invention continuously delivers oxybutynin throughout the entire gastrointestinal tract (GI), thereby making its therapeutically effective for oxybutynin to be absorbed throught the entire gastrointestional tract into the blood. That is, the controlled-extended release dosage form of this invention maintains a therapeutic plasma concentration substantively free of an overdose and substantially free of an ineffective underdose of oxybutynin.

In a multiple dose, crossover study, 13 healthy female volunteers of 41 to 68 years of age received either 5 mg of oxybutynin immediate release (IR) every 8 hours, or three 5 mg controlled release (CR) once a day, for four days. The patients blood was sampled on days 1 and 4 to quantify oxybutynin and its desethylmetabolite (DESOXY) by liquid chromatography mass spectroscopy (LC/MS). The oxybutynin was absorbed rapidly following immediate-release (IR) dosing with a mean $C_{max}$ of ng/ml. $C_{max}$ is the maximum concentration after dosing in the plasma. The drug release kinetics for the controlled-release (CR) plasma concentration rose slowly, reaching a mean $C_{max}$ value of 4.2–6.7 ng/ml. The metabolite DESOXY was formed rapidly following immediate release, and its formation parallelled the slow absorption of oxybutynin following controlled release. The DESOXY had a shorter $t_{1/2}$ life compared to OXY, indicating presystemic metabolite formation assuming it to be true metabolite $t_{1/2}$. Single and multiple dose AUC values were similar for both the controlled release and immediate release suggesting time invariant pharmacokinetics. AUC denotes the area under the plasma concentration profile. The 4 day OXY and DESOXY AUC and their ratios are presented in the Table below wherein BA denotes the percent bioavailable, that is, BA denotes the relative amount of oxybutynin absorbed from the controlled release (CR) dosage form compared to the immediate release (IR) dosage form, and $C_{max}$ denotes the maximum concentration.

|    | OXY (AUC) (ng · h/mL) | DESOXY (AUC) (ng · h/mL) | OXY/DESOXY Ratio | OXY (BA %) | DESOXY (BA %) |
|----|----|----|----|----|----|
| IR | 81  | 483 | 0.18 |     |    |
| CR | 109 | 304 | 0.41 | 153 | 69 |

The higher ratio of OXY-BA following CR compared to IR suggests lower metabolic formation on first pass. This indicates CR could reach the colon within 3–5 hours post dosing. Presystemic cytochrome P450-mediated oxidation may occur in the upper part of the gastrointestinal tract; then, drug release from CR in the colon escapes presystemic metabolism, which could explain the higher OXY/DESOXY ratio and increased OXY BA following CR.

The dosage form and the oxybutynin composition of this invention, as seen from the above disclosure, can be used in a method for administering a drug by the oral route, or the dosage form and composition can be sized and shaped for administering a drug by the sublingual and buccal routes. The sublingual and buccal routes can be used for quicker therapy, and they can be used when a smaller dose of drug is needed for immediate therapy. The latter routes can be used as a by-pass of the first pass of hepatic metabolism of the drug.

In summary, it will be appreciated that the present invention contributes to the art an unobvious dosage form that possesses practical therapeutic utility, and it can administer a drug at a dose-metered release rate per unit time.

We claim:

1. A method for the management of incontinence in a patient, wherein the method comprises admitting orally into the patient a dosage form comprising 240 ng to 650 mg of a member selected from the group consisting of oxybutynin and its pharmaceutically acceptable salt, that releases the member at a controlled and sustained, substantially zero order rate of 0.05 mg per hour up to 0.850 mg per hour for about 24 hours.

2. A pharmaceutical dosage form comprising 240 ng to 650 mg of a member selected from the group consisting of oxybutynin and its pharmaceutically acceptable salts, the dosage form being adapted to release the member at a controlled and sustained, substantially zero order release rate for about 24 hours.

3. A dosage form comprising 5 mg to 250 mg of a member selected from the group consisting of oxybutynin and its pharmaceutically acceptable salt, wherein (i) said dosage form provides a maximum plasma oxybutynin concentration of about 0.28 ng/ml to about 0.45 ng/ml per mg of said member in said dosage form and (ii) wherein said dosage form delivers said member from said dosage form over a period of about 24 hours.

4. The dosage form according to claim 3, wherein said salt is oxybutynin hydrochloride.

5. The dosage form of claim 4, wherein said dosage form delivers at a substantially zero order rate of release.

6. The dosage form according to claim 3, wherein said dosage form further comprises a member selected from the group consisting of hydroxypropylmethylcellulose, hydroxypropylethylcellulose, hydroxypropylbutylcellulose, and hydroxypropylpentylcellulose.

7. The dosage form according to claim 4, wherein said dosage form further comprises a member selected from the group consisting of hydroxypropylmethylcellulose, hydroxypropylethylcellulose, hydroxypropylbutylcellulose, and hydroxypropylpentylcellulose.

8. The dosage form of claim 3, wherein said dosage form delivers at a substantially zero order rate of release.

9. The dosage form according to claim 3, wherein said dosage form is a tablet.

10. The dosage form according to claim 4, wherein said dosage form is a tablet.

11. The dosage form according to claim 6, wherein said dosage form is a tablet.

12. The dosage form according to claim 7, wherein said dosage form is a tablet.

13. A method for the management of incontinence in a patient comprising administration to a subject of a dosage form comprising 5 mg to 250 mg of a member selected from the group consisting of oxybutynin and its pharmaceutically acceptable salt, wherein (i) said dosage form provides a maximum plasma oxybutynin concentration of about 0.28 ng/ml to about 0.45 ng/ml per mg of said member in said dosage form and (ii) wherein said dosage form delivers said member from said dosage form over a period of about 24 hours.

14. The method according to claim 13, wherein said salt is oxybutynin hydrochloride.

15. The method according to claim 13, wherein said dosage form further comprises a member selected from the group consisting of hydroxypropylmethylcellulose, hydroxypropylethylcellulose, hydroxypropylbutylcellulose, and hydroxypropylpentylcellulose.

16. The dosage form of claim 13, wherein said dosage form delivers at a substantially zero order rate of release.

17. The method according to claim 14, wherein said dosage form further comprises a member selected from the group consisting of hydroxypropylmethylcellulose, hydroxypropylethylcellulose, hydroxypropylbutylcellulose, and hydroxypropylpentylcellulose.

18. The dosage form of claim 17, wherein said dosage form delivers at a substantially zero order rate of release.

19. The method according to claim 13, wherein said dosage form is a tablet.

20. The method according to claim 14, wherein said dosage form is a tablet.

21. The method according to claim 15, wherein said dosage form is a tablet.

22. The method according to claim 17, wherein said dosage form is a tablet.

23. The method according to any one of claim 13, 14, 15, 17, 19, 20, 21 or 22 wherein the incidence of side effects associated with oxybutynin treatment is reduced.

* * * * *

US006919092C1

(12) EX PARTE REEXAMINATION CERTIFICATE (6480th)
United States Patent
Guittard et al.

(10) Number: US 6,919,092 C1
(45) Certificate Issued: Oct. 14, 2008

(54) METHOD FOR THE MANAGEMENT OF INCONTINENCE

(75) Inventors: George V. Guittard, Cupertino, CA (US); Francisco Jao, San Jose, CA (US); Susan M. Marks, San Jose, CA (US); David J. Kidney, Palo Alto, CA (US); Fernando E. Gumucio, San Jose, CA (US)

(73) Assignee: ALZA Corporation, Mountain View, CA (US)

Reexamination Request:
No. 90/007,772, Oct. 21, 2005

Reexamination Certificate for:
Patent No.: 6,919,092
Issued: Jul. 19, 2005
Appl. No.: 09/785,805
Filed: Feb. 16, 2001

Related U.S. Application Data

(63) Continuation of application No. 09/280,309, filed on Mar. 29, 1999, now Pat. No. 6,262,115, which is a continuation-in-part of application No. 08/806,773, filed on Feb. 26, 1997, now Pat. No. 5,912,268, which is a continuation-in-part of application No. 08/706,576, filed on Sep. 5, 1996, now Pat. No. 5,840,754, which is a continuation-in-part of application No. 08/445,849, filed on May 22, 1995, now Pat. No. 5,674,895.

(51) Int. Cl.
*A61K 9/00* (2006.01)
*A61K 31/216* (2006.01)
*A61K 9/20* (2006.01)
*A61K 31/221* (2006.01)
*A61K 31/21* (2006.01)

(52) U.S. Cl. .................. 424/464; 424/468; 514/534; 514/579; 514/646; 514/663; 514/727; 514/729; 514/730

(58) Field of Classification Search .................. None
See application file for complete search history.

(56) References Cited

U.S. PATENT DOCUMENTS

| 4,008,719 | A | 2/1977 | Theeuwes et al. ........... 128/260 |
|---|---|---|---|
| 4,519,801 | A | 5/1985 | Edgren ...................... 604/892 |
| 4,612,008 | A | 9/1986 | Wong et al. ................. 604/892 |
| 4,783,337 | A | 11/1988 | Wong et al. ................. 424/468 |
| 4,994,276 | A | 2/1991 | Baichwal et al. ............ 424/440 |
| 5,082,668 | A | 1/1992 | Wong et al. ................. 424/473 |
| 5,091,189 | A | 2/1992 | Heafield et al. ............. 424/457 |
| 5,128,143 | A | 7/1992 | Baichwal et al. ............ 424/464 |
| 5,135,757 | A | 8/1992 | Baichwal et al. ............ 434/465 |
| 5,178,868 | A | 1/1993 | Malmqvist-Granlund et al. .......................... 424/490 |
| 5,330,766 | A | 7/1994 | Morella et al. .............. 424/490 |
| 5,399,359 | A | 3/1995 | Baichwal .................... 424/464 |
| 5,407,686 | A | 4/1995 | Patel et al. ................. 424/468 |
| 5,455,046 | A | 10/1995 | Baichwal .................... 424/457 |
| 5,492,917 | A | 2/1996 | Rivero et al. ............... 514/319 |
| 5,498,422 | A | 3/1996 | Nakamichi et al. .......... 424/451 |
| 5,506,270 | A | 4/1996 | Upton et al. ................ 514/730 |
| 5,532,278 | A | 7/1996 | Aberg et al. ................ 514/617 |
| 5,591,452 | A | 1/1997 | Miller et al. ................ 514/468 |
| 5,674,895 | A | 10/1997 | Guittard et al. ............. 514/534 |
| 5,811,126 | A | 9/1998 | Krishnamurthy ............ 424/498 |
| 5,840,754 | A | 11/1998 | Guittard et al. ............. 514/534 |
| 5,874,107 | A | 2/1999 | Fischer et al. .............. 424/464 |
| 5,912,268 | A | 6/1999 | Guittard et al. ............. 514/534 |
| 5,945,123 | A | 8/1999 | Hermelin .................... 424/464 |
| 6,024,981 | A | 2/2000 | Khankari et al. ............ 424/464 |
| 6,031,003 | A | 2/2000 | Nemeth et al. .............. 514/579 |
| 6,056,968 | A | 5/2000 | Gilbert et al. ............... 424/422 |
| 6,068,859 | A | 5/2000 | Curatolo et al. ............ 424/490 |
| 6,071,970 | A | 6/2000 | Mueller et al. .............. 514/648 |
| 6,075,044 | A | 6/2000 | Wang et al. ................. 514/415 |
| 6,093,420 | A | 7/2000 | Baichwal .................... 424/468 |
| 6,096,339 | A | 8/2000 | Ayer et al. .................. 424/473 |
| 6,110,499 | A | 8/2000 | Shivanand et al. .......... 514/473 |
| 6,124,355 | A | 9/2000 | Guittard et al. ............. 514/534 |
| 6,129,930 | A | 10/2000 | Bova .......................... 424/468 |
| 6,262,115 | B1 | 7/2001 | Guittard et al. ............. 514/534 |

FOREIGN PATENT DOCUMENTS

| AU | 47732/90 | 7/1990 |
|---|---|---|
| WO | WO 96/37202 | 11/1996 |

OTHER PUBLICATIONS

Data Processed Using Dissprof Program (V1.1), Oxybutynin C1, Joint Exhibit 25, Nov. 24, 2003 Mylan 1014396–1014492.

Skelly, J.P. et al., "In Vitro and In Vivo Testing and Correlation for Oral Controlled/Modified–Release Dosage Forms", *Pharmaceutical Research*, 1990, 7(9), 975–977, Joint Exhibit 67.

Theeuwes, F. et al., Osmotic Delivery Systems for the β–Adrenoceptor Antagonists Metoprolol and Oxprenolol: Design and Evaluation of Systems for Once–Daily Administration, *Br. J. Clin. Pharmac.*, 1985, 19, 695–765, Joint Exhibit 81.

Oxybutynin, ALZA/TDC Meeting, Friday Jul. 15, 1993, Palo Alto, Ca. Defendant's Exhibits DX 00028, DXL–016926 thru DXL–016976.

Ballard, B.E., "Prolonged–Action Pharmaceuticals", Chapter 91, Defendant's Exhibit DX 00403, 1594–1613.

Corrigan, O.I. et al., "Influence of Dissolution Medium Buffer Composition on Ketoprofen Release from ER Products and in Vitro–in Vivo Correlation", *International Journal of Pharmaceutics*, 2003, 147–154, Defendant's Exhibit DX 00408.

Frick, A. et al., "Biopharmaceutical Characterization of Oral Controlled/Modified–Release Drug Products. In Vitro/in Vivo Correlation of Roxatidine", *European Journal of Pharmaceutics and Biopharmaceutics*, 1998, 46, 313–319, Defendant's Exhibits DX 00411.

(Continued)

*Primary Examiner*—Evelyn Huang

(57) ABSTRACT

A composition and a dosage form are disclosed comprising oxybutynin alone/or accompanied by another drug indicated for therapy. A method is disclosed for administering oxybutynin alone/or accompanied by a different drug or for administering oxybutynin and a different drug according to a therapeutic program for the management of incontinence alone, and for other therapy.

OTHER PUBLICATIONS

Drug Class Review on Urinary Incontinence Drugs, Final Report, Feb. 2003, Oregon Health & Science University, Defendant's Exhibit DX 00431.

Oregon Health Resources Commission, Urinary Incontinence (Update Report) Update #1, Mar. 2004, 12 pages, Defendant's Exhibit DX 00432.

Ouslander, J.G. et al., "Pharmacokinetics and Clinica Effects of Oxybutynin in Geriatric Patients", *The Journal of Urology*, 1988, 140, 47–50, Defendant's Exhibit DX 00433.

Qiu, Y. et al., "Once–a–Day Controlled–Release Dosage Form of Divalproex Sodium II: Development of a Predictive In Vitro Drug Release Method", *Journal of Pharmaceutical Sciences*, Nov. 2003, 92(11), 2317–2325, Defendant's Exhibit DX 00437.

ALZA Communication Exchange, A.C.E. Briefing, "The Making of Ditropan® XL: An Epic Celebrating the Cast of ALZAns who made it Happen, from 1993 to Today", Jan. 20, 1999, DXL–063089 thru DXL–063100, Defendant's Exhibit DX 00448.

Theeuwes, et al., "Elementary Osmotic Pump for Indomethacin", *Journal of Pharmaceutical Sciences*, Mar. 1983, 72(3), 253–258, Defendant's Exhibit DX 00450.

Thuroff, J.W. et al., "Randomized, Double–Blind, multi-center Trial on Treatment of Frequency, Urgency and Incontinence related to Detrusor Hyperactivity: Oxybutynin Versus Propantheline Versus Placebo", *The Journal of Urology*, Apr. 1991, 145, 813–817, Defendant's Exhibit DX 00453.

Welling, P.G., "In Vitro Methods to Determine Bioavailability: In Vitro–In Vivo Correlations", 223 thru 232, Defendant's Exhibits DX 00462.

Executive Summary, OROS® (Oxybutynin Chloride) CPC–1, Oct. 1997, DXL–031021 thru DXL–063202, Defendant's Exhibit DX 01079.

Stage 0: Product Concept Assessment Form Synopsis, Mar. 2, 1993, DXL–063198 thru 063202, Defendant's Exhibits DX 01143.

Ditropan Xl and Market Pricing, Defendant's Exhibit DX 01151, JJ–00447 thru JJ–00456.

Harry C. Boghician (Portfolio), 5 pages Defendant's Exhibit DX 1216 A.

In the United States District Court for the Northern District of West Virginia, *ALZA Corporation*, Plantiff v. *Mylan Laboratories, Inc., Mylan Pharmaceuticals, Inc.* Defendants, C.A. No. 1:03CV61, Expert Report of James A. Forstner, Apr. 29, 2004, Defendant's Exhibit DX 01219.

Curriculum Vitae—Gordon L. Amidon, Defendant's Exhibit DX 01226, 93 pages.

Fax Letter from Jeffrey I.D. Lewis to James H. Wallace, Defendant's Exhibit DX 01245, 2 pages.

Curriculum Vitae, Stanley Kandzari, M.D. Updated Apr. 1, 2005, Defendant's Exhibit DX 1266 VB, 1 page.

Experimental Formula Sheet–Sustained Release Oxybutynin Chloride Pellets, MYLAN 1014435, Defendant's Exhibit DX 01403.

Australia Patents Act, Complete Specification for Sustained Release Pharmaceutical Composition, 55 pages.

Saks, S.R. MD, "Pharmacokinetics of OROS® and Oxybutynin", *ALZA Corporation Physician Advisory Board Meeting*, Oct. 9–11, 1998, DXL–044580 thru 004591 Defendant's Exhibit DX 1501.

Winkler, H.A. et al., "Treatment of Detrusor Instability with Oxybutynin Rectal Suppositories" *International Urogynecology Journal*, 1998, 9, 100–102, Defendant's Exhibit DX 1503, 3 pages.

Massad, C.A. et al., "The Pharmacokinetics of Intravesical and Oral Oxybutynin Chloride", *The Journal of Urology*, 1992, 148, 595–597, Defendant's Exhibit DX 1504.

Defendant's Exhibit DX 1507, DXL084950 thru DLX084985.

Projected Ditropan Xl Net Trade Sales, Defendant's Exhibit DX 1511, 5 pages.

Quarterly TRX Market Share and TRX Following Launch-(Quarterly), Defendant's Exhibits DX 1512.

Gupta, S. PhD., New Pharmacokinetic Information on Ditropan® XL, *Physician Advisory Board Meeting, Medical Education Technologies Job #AZ11–0013*, Defendant's Exhibit DX 1515C, DXL 045275 thru 045313.

Stage 0: Product Concept Assessment Form Snyopsis, Mar. 2, 1993, Defendant's Exhibit DX 1517, DXL 063216 thru 063222.

Final Report C–96–074–02 "Effect of Food on the Pharmacokinetics and Bioavailability of OROS® (oxybutynin chloride) relative to Ditopan®", Nov. 1997, DXL–081963 thru 081999, Defendant's Exhibit DX 1530.

Oxybutynin Chloride, Defendant's Exhibit DX 1540, DXL 050624 ,050505 thru 050516, 9 pages.

Oxybutynin Chlroide, Defendant's Exhibit DX 1541, DXL 050625, 1 page.

Defendant's Exhibit DX 1542, 1 page.

Defendant's Exhibit DX 1543, ALZA Expert 00267, 1 page.

Genitourinary Smooth Muscle Relaxants, *American Hospital Formulary Service*, 1997, Defendant's Exhibit DX 1544, DXL 079384 thru DXL 0793387.

Letter from Jeffrey I.D. Lewis to Nicholas A Peppas, Ph.D., Defendant's Exhibits 1546, 5 pages.

In the United States District Court for the Southern District of Florida, *Pfizer, Inc. and Alza Corporation*, Plaintiffs, v. *Andrx Corporation, Andrx Pharmaceuticals, inc. and Andrx Pharmaceuticals, LLC*, Defendants, C.A. No. 01–8636, Amended Complaint, Defendant's Exhibit DX 1548, 17 pages.

Siepmann, J. et al., "HPMC–Matrices for Controlled Drug Delivery: A New Model Combining Diffusion, Swelling, and Dissolution Mechanisms and Predicting the Release Kinetics", *Pharmaceutical Research*, 1999, 16(11), 1748–1756, Defendant's Exhibit DX 1551.

Siepman, J. et al., "A New Model Describing the Swelling and Drug Release Kinetics from Hydroxypropyl Methylcellulose Tablets", *Journal of Pharmaceutical Sciences*, Jan. 1999, 88(1), 65 thru 72, Defendant's Exhibit DX 1552.

Baker, R., "Controlled Release of Biologically Active Agents", 1987, 1–21, Defendant's Exhibit DX 1553.

'355 Claim 1 vs. Baichwal Example 15 Data, 1 page, Defendant's Exhibit 1554.

'355 Claim 1 vs. Baichwal Example 15 vs. Example 1, 1 page, Defendant's Exhibit 1557.

Fundamentals of Controlled Release and Pharmaceutical Engineering, Spring 1993, Defendant's Exhibit DX 1558.

'355 Claim 1 vs. '355 Example 1 Data, Defendant's Exhibit DX 1559, 1 page.

U.S. Pharmacopeia & National Formulary, Defendant's Exhibit DX 1561, 2232–2240.

Figure 1 of the '355 Patent: Typical Release Curve for 24–Hour Controlled Release Data, Defendant's Exhibit DX 1562, 1563 2 pages.

General Requirements for Tests and Assays, Defendant's Exhibit DX 1566, 1833 thru 1861.

Moore, K. et al., "Oxybutynin Hydrochloride (3mg) in the Treatment of Women with Idiopathic Detrusor Instability", *British Journal of Urology*, 1990, 66, 479–485, Defendant's Exhibit DX 1570.

USP Dissolution Calibrator, Non–Disintegrating Type, Defendant's Exhibit DX 1573, 2 pages.

Oxybutynin Chloride ER (OXYB–0262) Data, Defendant's Exhibit DX 1580–DX 1586, Mylan 0060307, 1 page.

Reviewer Guidance–Validation of Chromatographic Methods, *Center for Drug Evaluation and Research (CDER)*, Nov. 1994, 1 thru 30, Defendant's Exhibit 1588.

Drug Release Profile Data—Defendant's Exhibit DX 1589, MYLAN 1014490–1014492.

Drug Release Profile Data—Defendant's Exhibit DX 1590, MYLAN 1014485–1014487.

Drug Release Profile Data—Defendant's Exhibit DX 1591, MYLAN 1014477–1014479.

Drug Release Profile Data—Defendant's Exhibit DX 1592, MYLAN 1014480–1014482.

ALZA Corporation—Payments to Virginia Commonwealth University Data—Defendant's Exhibit 1593, DXL 085000–085017.

Mylan 10 mg Product—Apparatus 2(Paddle) with Media Switch Data—Defendant's Exhibit DX 1594–1598.

U.S. Pharmacopeia & National Formulary, Defendant's Exhibit DX 1803, 1128–1129.

Baichwal Teaches the Conventional Wisdom Data—Defendant's Exhibit DX 1804, 1 page.

Mylan 5mg Product Data—Defendant's Exhibit DX 1805, 7 pages.

Mylan 10 mg Product Data—Defendant's Exhibit DX 1806, 4 pages.

Concentration Result Data—Defendant's Exhibit DX 1808, 1 page.

U.S. Pharmacopeia—The Official Compendia of Standards, Defendant's Exhibit 1814, 4 pages.

Mylan 10 mg Product, Mylan 5 mg Product Data—Defendant's Exhibit DX 1816–1817.

U.S. Pharmacopeia—The Official Compendia of Standards, Defendant's Exhibit 1818, 6–8, 2160–2165.

Mylan 10 mg Product Data—Defendant's Exhibit DX 1819, 1 page.

U.S. Pharmacopeia—The Official Compendia of Standards, Defendant's Exhibit 1821, 2513–2519.

CD—Defendant's Exhibit DX 1822.

'355 Claim 1 vs. Examples A and B Data—Defendant's Exhibit 1823, 1 page.

Data—Defendant's Exhibit 1825, 1 page.

Mylan Tablet Data—Defendant Exhibits 1827 thru 1831.

5 mg Oral Solution Data—Defendant's Exhibit 1832–1833, 46 pages.

Mylan Tablet Data—Defendant's Exhibit 1836, 1 page.

Mylan Tablet Data—Defendant's Exhibit 1900–1901.

Miyamoto, E. et al., "Physico–Chemical Properties of Oxybutynin", *Analysts*, Jul. 1994, 119, 1489–1492, Defendant's Exhibit 1902, DXL 005871–005874.

State of the Art: Colonic Absorption Studies, Defendant's Exhibit DX 2001, 1 page.

Colonic Absorption Studies and Data—Defendant's Exhibit DX 2002.

Wong, P.S.L. et al., "Osmotically Controlled Tablets", *Modified–Release Drug Delivery Technology*, 2003, 101–114 Joint Exhibit 109.

ALZA: OROS® Oral Delivery Technology, Mar. 9, 2004, http://www.alza.com/print/oros, Joint Exhibit 111, 2 pages.

Patent Information: Ditropan XL® (oxybutynin chloride) Extended Release Tablet, Joint Exhibit 112, DXL 070943.

Douchamps, J. et al., "The Pharmacokinetics of Oxybutynin in Man", *Eur J. Clin Pharmacol*, 1988, 35, 515–520, Joint Exhibit 116, 5 pages.

Cystrin® SR, Sustained Release Oxybutynin Hydrochloride, Development Pharmaceutics, Mar. 9, 1994, PW 000225–PW 000280, Joint Exhibit 130.

Patent Data, DXL 070941–070942, Joint Exhibit 131.

The United States Pharmacopeia Convention, Inc. 1990, 1790–1799, Joint Exhibit 133.

Oxybutynin/Official Monographs, Joint Exhibit 134, 1 page.

The United States Pharmacopeia Convention, Inc., The Official Compendia of Standards, 2002, 2010–2022, Joint Exhibit 135.

Joint Exhibit 137, 1578–1581.

Van Bommel, E.M.G. et al., Comparison of In Vitro and In Vivo Release Characteristics of Acetaminophen from Gradient Matrix Systems, *Biopharmaceutics & Drug Disposition*, 1991, 12, 367–373, Joint Exhibit 139.

Oxybutynin Chloride Extended–Release Tablets, 10 MG, Uniformity of Dosage Units (FP–OXYB10–CU–M), 5514–5539, Mylan 0065620–0065646, Joint Exhibit 232.

Preik, M. et al., "Effect of Controlled–Release Delivery on the Pharmacokinetics of Oxybutynin at Different Dosages: Severity–Dependent Treatment of the Overactive Bladder", *BJU International*, 2004, 821–827, Plaintiff's Exhibit 396.

Patent Data, Plaintiff's Exhibit 40, 43, 53, 54, 58, 59, 1 page each, 6 total pages.

Leesman, G.D. et al., "Simulation of Oral Drug Absorption: Gastric Emptying and Gastointestinal Motility", *Pharmacokinetics*, Chapter 6, 267–284, Plaintiff's Exhibit 131.

Patent Data, Plaintiff's Exhibit 143, 1 page

Product Monograph, Once–a–Day Ditropan® XL, Plaintiff's Exhibits 157, DXl–044976 thru DXL–045027.

Anderson, R.U. et al., "Once Daily Controlled Versus Immediate Release Oxybutynin Chloride for Urge Urinary Incontinence", *The Journal of Urology*, Jun. 1999, 161, 1809–1812, Plaintiff's Exhibit 197.

Versi, E. MD, PhD. Et al., "Dry Mouth with Conventional and Controlled Release Oxybutynin in Urinary Incontinence", *Obstetrics & Gynecology*, 2000, 95(5), 718–721, Plaintiff's Exhibit 198.

Appell, R.A. MD. et al., "Prospective Randomized Controlled Trial of Extended–Release Oxybutynin Chloride and Tolterodine Tartrate in the Treatment of Overactive Bladder: Results of the Object Study", *May Clin. Proc.*, 2001, 76, 358–363, Plaintiff's Exhibit 199.

OROS TDC–1 Meeting Minutes, Nov. 23, 1993, DXL–027199–02713, Plaintiff's Exhibit 203.

Cystrin Cr–Release Rate Profile, Aug. 14, 1998, DXL–017224–017225, Plaintiff's Exhibit 213.

Patent Data–DXL 016934, Plaintiff's Exhibit 260.

Gupta, S.K. PhD. et al., "Pharmacokinetics of an Oral Once–a–Day Controlled–Release Oxybutynin Formulation Compared with Immediate–Release Oxybutynin", *J. Clin. Pharmacol*, 1999, 39, 289–296, DXL–023945–023952, Plaintiff's Exhibit 261.

Patent Data, MYLAN 1008193–1008196, Plaintiff's Exhibit 266.

Highlights of OROS TDC–1 Meeting, Jun. 28, 1993, DXL 017162, Plaintiff's Exhibit 287.

OROS TDC–1 Meeting Minutes—Sep. 17, 1993, DXL 027224–027236, Plaintiff's Exhibit 288.

Work Plan and Cost Estimate for Stage 2 Activities for OROS® Oxybutynlin, DXL 043711–043715, Plaintiff's Exhibit 289.

Commercial Assessment OROS/TTS TDC–1 Oxybutynin, Stage 3, Sep. 1995, DXL 063416–063563, Plaintiff's Exhibit 308.

OROS TDC–1 Meeting Minutes, Oct. 21, 1993, DXL 027214–027215, Plaintiff's Exhibit 309.

Sathyan, G. et al., "Effect of OROS® Controlled–Release Delivery on the Pharmacokinetics and Pharmacodynamics of Oxybutynin Chloride", *J. Clin. Pharmacol*, 2001, 52, 409–417, DXL 051995–052003, Plaintiff's Exhibit 315.

Buyse, G. et al., "Intravesical Pxybutynin for Neurogenic Bladder Dysfunction: Less Systemic Side Effects Due to Reduced First Pass Metabolism", *The Journal of Urology*, 1998, 160, 892–896, Plaintiff's Exhibit 323.

Diokno, A.C. et al., "Prospective, Randomized, Double–blind Study of the Efficacy and Tolerability of the Extended–Release Formulations of Oxybutynin and Toltero- dine for Overactive Bladder: Results of the OPERA Trail", *Mayo Clin Proc.*, 2003, 78, 687–695, Plaintiff Exhibit 326.

Gupta, P. K. et al., "Oral Controlled–Release Delivery", *Treatise on Controlled Drug Delivery*, 1992, PX329_ 0002–329_0058, Plaintiff's Exhibit 329.

Dmochowski, R.R. et al., "Advancements in Pharmacologic Management of the Overactive Bladder", *Urology*, 2000, 54(6A), 41–49, Plaintiff's Exhibit 391.

Read, N.W. et al., "Gastrointestinal Dynamics and Pharma- cology for the Optimum Design of Controlled–Release Oral Dosage Forms", *CRC Critical Reviews in Therapeutic Drug Carrier Systems*, 1987, 4(3), 221–263, Plaintiff's Exhibits 397.

Miyamoto, E. et al., "Physico–Chemical Properties of Oxy- butynin", *Analyst*, 1994, 119, 1489–1492, DXL 005871–005874.

Modern Pharmaceutics, Oral Drug Delivery, Chapter 5, ALZA Research Library, DXL 043878 thru DXL 043926, Plaintiff's Exhibit 403.

Physicians' Desk Reference®, PDR®, 47$^{th}$ Edition, 1993, 1377–1378, DXL 028121–DXL 028123, Plaintiff's Exhibit 451.

Longer, M.A. et al., "Sustained–Release Drug Delivery Sys- tems", *Pharmaceutical Sciences*, 1985, 92, 1644–1661, Plaintiff's Exhibit 462.

Patent Data, JJ 00142 thru JJ 00281, Plaintiff's Exhibit 464.

Banker, G.S., "Pharmaceutical Applications of Controlled Release: An Overview of the Past, Present, and Future", *Medical Applications of Controlled Release*, 1984, vol. II, 1–34, Plaintiff's Exhibit 467.

Yu, L.X. et al., "Transport Approaches to the Biopharmaceu- tical Design of Oral Drug Delivery Systems: Prediction of Intestinal Absorption", *Advanced Drug Delivery Reviews*, 1996, 19, 359–367, Plaintiff's Exhibit 471.

Lipka, E. et al., "Setting Bioequivalence Requirements fro Drug Development based on Preclinical Data: Optimizing Oral Drug Delivery Systems", *Journal of Controlled Release*, 1999, 62, 41–49, Plaintiff's Exhibit 473.

Lukkari, E. et al., "Effect of Food on the Bioavailability of Oxybutynin from a Controlled Release Tablet", *Eur. J. Clin. Pharmacol.*, 1996, 50, 221–223, Plaintiff's Exhibit 482.

Rocca, J. G. PhD. et al., "Oral Drug Delivery: Prospects & Challenges", *Drug Delivery Technology*, 2004, 4(4), 53–57, Plaintiff's Exhibit 484.

Waldeck, K. et al., "Comparison of Oxybutynin and its Active Metabolite, N–Desethyl–Oxybutynin, in the Human Detrusor and Parotid Gland", *The Journal of Urology*, 1997, 157, 1093–1097, Plaintiff's Exhibit 486.

Chancellor, M.B. Md, et al., "A Comparison of the Effects on Saliva Output of Oxybutynin Chloride and Tolterodine Tartrate", *Clinical Therapeutics*, 2001, 23(5), 753–760, Plaintiff's Exhibit 488.

Laboratory Notebook, Biomaterials & Drug Delivery Labs, Plaintiff's Exhibit 491.

Patent Data—Plaintiff's Exhibit 494 (d).
Patent Data—Plaintiff's Exhibit 495 (e).
Patent Data—Plaintiff's Exhibit 496 (f).
Patent Data—Plaintiff's Exhibit 497 (g).

*Alza Corporation* v. *Mylan Laboratories, Inc. and Mylan Pharmaceuticals, Inc*, No. 1:03cv61–Supplemental Expert Report of Anthony Lowman, Lowman Video, Plaintiff's Exhibit 498 (h), 1 page copy of the disc only.

Stage 0: Product Concept Assessment Form Synopsis, Mar. 2, 1993, DXL–016939 thru 016948, Plaintiff's Exhibit 503.

Translation of Finnish Package Insert (from Swedish lan- guage), DXL 012241–012243, Plaintiff's Exhibit 506.

Patent Data—JJ 02815 thru JJ 02817, Plaintiff's Exhibit 536, 538.

Patent Data—Plaintiff's Exhibit 548, 549, 550, 551.

Curriculum Vitae of Nicholas A. Peppas, 1–113, Plaintiff's Exhibit 552.

General Information—In Vitro and In Vivo Evaluation, *The United States Pharmacopeia Convention, Inc.*, 2161, Plain- tiff's Exhibit 554.

Patent Data—Drug Release Profile—Plaintiff's Exhibit 555, MYLAN 1014477–1014492.

Curriculum Vitae of Anthony M. Lowman, Ph.D., 15 pages, Plaintiff's Exhibit 556.

Chancellor, M.B. et al., "Spit Study to Compare Different Formulations of Oxybutynin", Accepted as Poster Presenta- tion at 1999 AUA, Plaintiff's Exhibit 561, DXL 048067, Plaintiff's Exhibit 561.

Gittleman, M. et al., "Once–Daily Oxybutynin Chloride (Ditropan XL) in Patients on other Anticholinergic Medica- tions", Accepted as Poster Presentation at 1999 AUA, Plain- tiff's Exhibit 562, DXL 048068.

Sand, P. Md. et al., "Dose Titration with Once–Daily Oxybu- tynin Chloride (Ditropan XL) in Previously Treated and Naive Patients", Accepted as Oral Presentation at 1999 ACOG, Plaintiff's Exhibit 563, DXL 048071.

Versi, E. Md. et al., Improving Urge Incontinence Treat- ments by Decreasing Dry Mouth with Controlled–Release Oxybutynin (Ditropan XL), Accepted as Poster Presentation at 1999 ACOG, Plaintiff's Exhibit 566, DXL 048072.

Schmidt, R.A., "Efficacy of Controlled–Release Once–a–Day Oxybutynin Chloride for Urge Urinary Incon- tinence", *Division of Urology*, Plaintiff's Exhibit 567, DXL 048073.

Brown, J., "Comparison of tolerability and Efficacy of Once–a–Day vs. Immediate–Release Oxybutynin Chloride in Patients with Urge Urinary Incontinence", 1998, Plaintiff's Exhibit 569, DXL 048078.

Michel, M.C., "A Benefit–Risk Assessment of Extended–Release Oxybutynin" Drug Safety, 2002, 25(12), 867–876, Plaintiff's Exhibit 570.

Physicians' Desk Reference®, 1994, 48 edition, 20, Plaintiff's Exhibit 577.

Oxybutynin Chloride Extended Release Tablets 10 mg, Finished Product Specifications, MYLAN 0046025–0046026, Plaintiff's Exhibit 579.

Patent Data—MYLAN 1006248–1006257, Plaintiff's Exhibit 591.

Patent Data—Plaintiff's Exhibit 592, 593, 594, 595.

Patent Data—Experimental Formula Sheet—MYLAN 1014435–1014466, Plaintiff's Exhibit 596.

Qureshi, S.A. et al., "Typical Variability in Drug Dissolution Testing: Study with USP and FDA Calibrator Tablets and a Marketed Drug (Glibenclamide) Product", European Journal of Pharmaceutical Sciences, 1999, 7, 249–258, Plaintiff's Exhibits 598.

Patent Data—Plaintiff's Exhibit 602 thru 649.

Curriculum Vitae—Michael B. Chancellor, M.D., 83 pages, Plaintiff's Exhibit 650.

Goldenberg, M.M. PhD. "An Extended Release Formulation of Oxybutynin Chloride for the Treatment of Overactive Urinary Bladder", Clinical Therapeutics, 1999, 21(4), 634–642, DXL 052302–052031, Defendant's Exhibit 656.

Ouslander, J.G. MD., "Management of Overactive Bladder", The New England Journal of Medicine, 2004, 350, 786–799, Plaintiff's Exhibit 664.

Abrahamsson, B. et al., "Absorption, Gastrointestinal Transit, and Tablet Erosion of Felodipine Extended–Release (ER) Tablets", Pharmaceutical research, 1993, 10(5), 709–714.

Artursson, P., "Epithelial Transport of Drugs in Cell Culture. I: A Model for Studying the Passive Diffusion of Drugs over Intestinal Absorptive (Caco–2) Cells", Journal of Pharmaceutical Sciences, Jun. 1990, 79(6), 476–482.

Chao, S.T. et al., "Effect of Food on Bioavailability of Pseudoephedrine and Brompheniramine Administered from a Gastrointestinal Therapeutic System", Journal of Pharmaceutical Sciences, 1991, 80(5), 432–435.

Chung, M. PhD. et al. "Clinical Pharmacokinetics of Nifedipine Gastrointestinal Therapeutic System", The American Journal of Medicine, 1987, 83, 10–14.

Davis, S.S. et al., "Relationship between the rate of Appearance of Oxprenolol in the Systemic Circulation and the Location of an Oxprenolol Oros 16/260 Drug Delivery System within the Gastrointestinal Tract as Determined by Scintigraphy", Br. J. Clin. Pharmac, 1988, 26, 435–443.

Harder, S. et al., "Ciprofloxacin Absorption in Different Regions of the Human Gastrointestinal Tract. Investigations with the hf–Capsule", Br. J. Clin. Pharmac., 1990, 30, 35–39.

Hirtz, J., "The Absorption Window; Fact or Fiction?", Pharmacy International, 1984, 175–178.

Marathe, P.H. et al., "Absorption and Presystemic Metabolism of Nefazodone Administered at Different Regions in the Gastrointestinal Tract of Humans", Pharmaceutical Research, 1995, 12(11), 1716–1721.

Riley, S.A. et al., "Absorption of Polar Drugs following Caecal Instillation in Healthy Volunteers", Aliment Pharmacol Ther., 1992, 6, 701–706.

Sandberg, A. et al., "Steady–State Bioavailability and Day–to–Day Variability of a Multiple–Unit (CR/ZOK) and a Single–Unit (OROS) delivery System of Metoprolol after Once–Daily Dosing", Pharmaceutical Research, 1993, 10(1), 28–34.

Stiehl, A. et al., "Colonic Absorption of Ursodeoxycholic Acid in Man", 42, 323–325.

Wilding, I.R. et al., "Gastrointestinal Transit and Systemic Absorption of Captopril from a Pulsed–Release Formulation", Pharmaceutical Research, 1992, 9(5), 654–657.

Williams, M.F. et al., "Influence of Gastrointestinal Site of Drug Delivery on the Absorption Characteristics of Ranitidine", Pharmaceutical Research, 1992, 9(9), 1190–1194.

Wilson, C.G. et al., "Bimodal release of Ibuprofen in a Sustained–Release Formulation: A Scintigraphic and Pharmacokinetic Open Study in Healthy Volunteers under Different Conditions of Food Intake", International Journal of Pharmaceutics, 1989, 50, 155–161.

Antonin, K–H., "Other Methods in Studying Colonic Drug Absorption", Chapter 5, 89–107.

Antonin, K.H. et al., "Evaluation of the Colonic Drug Absorption in Patients with an Artificial Intestinal Stoma and by Colonoscopy in Normal Volunteers", National Library of Medicine, 39–52.

Bieck, P.R., "Drug Absorption from the Human Colon", Acta Pharm Technol, 1987, 33, 109–114.

Davis, S.S., "Assessment of Gastrointestinal Transit and Drug Absorption", Drug Delivery and its Therapeutic Application, 1989, 9, 89–101.

Hirtz, J.K "Intubation Techniques for the Study of the Absorption of Drugs in Man", National Library of Medicine, 3–12.

Hirtz, J., "The Gastrointestinal Absorption of Drugs in Man: A Review of Current Concepts and Methods of Investigation", Br. J. Clin. Pharmac, 1985, 19, 77S–83S.

Schuster, O. et al., "Course of Development of the HF–Capsule–Variations and Method–Related Typical Findings", National Library of Medicine, 28–38.

Colonic Absorption Review Articles, Defendant's Exhibit DX 2003, 1 page.

Fara, J.W., "Colonic Drug Absorption and Metabolism", Novel Drug Delivery and its Therapeutic Application, 1989, 10, 103–112, Defendant's Exhibit DX 2004.

Summary of Dr. Dmochowski's ALZA Contracts, Defendant's Exhibit DX 2005.

Summary of Dr. Chancellor Contracts, Defendant's Exhibit DX 2006.

Alza Total Payments to Dr. Chancellor, Defendant's Exhibit DX 2007 and DX 2007 A.

Articles Regarding First–Pass Metabolisms, Defendant's Exhibit DX 2008, 1 page.

Articles Regarding Reduced Side Effects from Non–Oral Administration, Defendant's Exhibit DX 2009, 1 page.

Aaltonen, L. et al., "Antimuscarinic Activity of Oxybutynin in the Human Plasma Quantitated by a Radioreceptor Assay", Acta Pharmacol. Et Toxicol, 1984, 55, 100–103.

Hughes, K.M. et al., "Measurement of Oxybutynin and its N–Desethyl Metabolite in Plasma and its Application to Pharmacokinetic Studies in Young, Elderly and Frail Elderly Volunteers", Xenobiotica, 1992, 22(7), 859–869.

Abstracts of the 1st Congress of the European Association for Clinical Pharmacology and Therapeutics, 1995, *Thérapie*, 65–68, Plaintiff's Exhibit 485.

Madersbacher, H. Md. et al, "Control of Detrusor Hyperreflexia by the Intravesical Instillation of Oxybutynine Hydrochloride", *Paraplegia*, 1991, 29, 84–90.

Ditropian Xl, Prescribing Information, Joint Exhibit 239, 2 pages.

OROS Oxybutynin Release Rates Patent Data—Joint Exhibit 27.

OROS Oxybutynin Release Rates Patent Data—Joint Exhibit 28.

OROS Oxybutynin Release Rates Patent Data Patent Data—Joint Exhibit 29.

OROS Oxybutynin Release Rates Patent Data Patent Data—Joint Exhibit 30.

OROS Oxybutynin Release Rates Patent Data Patent Data—Joint Exhibit 31.

OROS Oxybutynin Release Rates Patent Data Patent Data—Joint Exhibit 32.

OROS Oxybutynin Release Rates Patent Data Patent Data—Joint Exhibit 33.

OROS Oxybutynin Release Rates Patent Data Patent Data—Joint Exhibit 35.

Appendix D—List of Documents Reviewed—Joint Exhibit 47.

Alza Corp. v. Mylan, C.A. # 1:03CV61, Expert Report of Dr. Gordon Amidon, Appendix J: Photo of Different Dosage Forms CD, Joint Exhibit 53.

Lish, P.M., "Oxybutynin–A Musculotropic Antispasmodic Drug with Moderate Anticholinergic Action", *Mead Johnson Research Center*, 1964, 467–488, DXL 014384–014406, Joint Exhibit 54.

Experimental Formula Sheet Patent Data—MYLAN 1014326–1014370, Joint Exhibit 55.

Declaration of Dr. William Barr, Joint Exhibit 56, 7 pages.

Declaration of Dr. Patrick S.L. Wong, Joint Exhibit 57, 14 pages.

Draft Annotated Physician Insert–Ditropan® XL, DXL 072395–DXL 072407, Joint Exhibit 78.

Rovner, E.S., et al., "Once–Daily, Extended–Release Formulations of Antimuscarinic Agents in the Treatment of Overactive Bladder: A Review", *European Urology*, 2002, 41, 6–14, Joint Exhibit 84.

Guidance for Industry, Extended Release Oral Dosage Forms: Development, Evaluation, and Application of In/Vitro/In Vivo Correlations, *U.S. Dept. of Health and Human Services Food and Drug Administration Center for Drug Evaluation and Research*, Sep. 1997, 1–24, Joint Exhibit 86.

Pitsiu, M. et al., "A Semiparametric Deconvolution Model to Establish in Vivo–In Vitro Correlation Applied to OROS Oxybutynin", *Journal of Pharmaceutical Sciences*, 2001, 90(6), 702–712, Joint Exhibit 89.

Barr Affidavit, 1–23, Joint Exhibit 90.

Letter from S. Wayne Talton to Gary J. Buehler, re: Oxybutynin Chloride Extended–Release Tablets, 10mg and 76–644 Response to Agency Correspondence dated Dec. 8, 2003, MYLAN 0978814–097835 w attached patent data, Joint Exhibit 91.

Theeuwes, F., "Evolution and Design of Rate Controlled Osmotic Forms", *Current Medical Research and Opinion*, 1983, 8(2), 20–27, Joint Exhibit 93.

Theeuwes, F., et al. "Systems for Triggered, Pulsed, and Programmed Drug Delivery", *Annals New York Academy of Science*, 428–440, Joint Exhibit 94.

Peters, K.M. et al., "Urinary Incontinence", 685–688, Joint Exhibit 95.

Yarker, Y.E. et al., "Oxybutynin–A review of its Pharmacodynamic and Pharmacokinetic Properties, and its Therapeutic Use in Detrusor Instability", *Drug and Aging*, 1993, 3, 243–262, Joint Exhibit 96.

Hughes, K.M. et al., "Measurement of Oxybutynin and its N–Desethyl Metabolite in Plasma, and its Application to Pharmacokinetic Studies in Young, Elderly and Frail Elderly Volunteers", *Xenobiotica*, 1992, 22(7), 859–869, Joint Exhibit 97.

Robinson, T.G. et al., "Drugs in Focus: Oxybutynin Hydrochloride", *Prescribers' Journal*, 1994, 34(1), 27–31, Joint Exhibit 98.

Katori, N. et al., "Estimation of Agitation Intensity in the GI Tract in Humans and Dogs Based on in Vitro/in Vivo Correlation", *Pharmaceutical Research*, 1995, 12(2), 237–243, Joint Exhibit 99.

Lukkari, E. et al., "Effect of Time Interval between Food and Drug Ingestion on the Absorption of Oxybutynin from a Controlled–Release Tablet", *Pharmacology & Toxicology*, 1997, 81, 31–34, DXL 005964–005967 Joint Exhibit 101.

Declaration of Dr. Patrick S.L. Wong, Joint Exhibit 107, 28 pages.

Declaration of Dr. William Barr, Joint Exhibit 108.

Patent Data—Ditropan XL 2003 OE/2004BP/2005 Forecast, JJ 00497–00577, Plaintiff's Exhibit 139.

Collas, D. et al., "The Pharmacokinetic Properties of Rectal Oxybutynin—a Possible Alternative to Intravesical Administration", *Neurourology and Urodynamics*, 1997, 16(5), 346–347.

Madersbacher, M. et al., "Intravesical Application of Oxybutynine: Mode of Action in Controlling Detrusor–Hyperreflexia", *Dept. Urology, Univ. Hosp. Innsbruck and Rehab Center*, 375–376.

Mizunaga, M, Md. et al., "Intravesical Instillation of Oxybutynin Hydrochloride Therapy for Patients with a Neuropathic Bladder", *Paraplegia*, 1994, 32, 25–29.

Weese, D.L. et al., "Intravesical Oxybutynin Chloride: Experience with 42 Patients", *Urology*, Jun. 1993, 41(6), 527–530.

O'Flynn, K.J. et al., "Intravesical Instillation of Oxybutynin Hydrochloride for Detrusor Hyper–Reflexia", *British Journal of Urology*, 1993, 72, 566–570.

Remington's Pharmaceutical Sciences, "Pharmacokinetic Models", 36, 726.

Lukkari, E., "Clinical Pharmacology of Oxybutynin, with Special Reference to Pharmacokinetics and Interactions", *Department of Clinical Pharmacology*, 1997, 1–50, PW 000281–000331.

Nilsson, C.G. et al. "Comparison of a 10–mg Controlled Release Oxybutynin Tablet with a 5–mg Oxybutynin Tablet in Urge Incontinent Patients", *Neurourology and Urodynamics*, 1997, 16, 553–542, DXL 012130–012139.

"Cystrin CR Launched in Finland for Urinary Incontinence", *Doctor's Guide to Medical & Other News*, http://www.pslgroup.com, May 7, 1998, 2 pages.

Fincher, J.H., "Particle Size of Drugs and its relationship to Absorption and Activity", *J. Pharm. Sci.*, 1968, 57, 1825–1835.

King, R.E. PhD. et al., "Oral Solid Dosage Forms", *Pharm. Sci. by Remington*, 17$^{th}$ Ed., Ch. 90, pp. 1603–1625 (1985), published by Mack Publishing.

Linhardt, R.J., "Biodegradable Polymers for Controlled Release of Drugs", Edited by M. Rosoff, Ch 2, pp. 53–95 (1989).

Riva, D. et al., Oxybutynin Chloride in the Treatment of female Idiopathic ladder Instability, *Clin. Exp. Obst. Gyn*, 1984, 37–42.

Coleman, M.M et al., "A Practical Guide to Polymer Miscibilit", *Polymers*, 31, 1187–1231 (1990).

Drug Carrier Systems, by Roerdink et al., vol. 9, pp. 57–109 (1989).

Leong, K.W. et al., "Polymeric Controlled Drug Delivery", *Advanced Drug Delivery Reviews.*, vol. 1, 199–233 (1987).

Handbook of Common Polymers, Compiled by Roff et al., (1971), published by CRC Press, 72–81.

Wurster, D.E., "Air–Suspension Technique of Coating Drug Particles," *Journal of the American Pharmaceuticl Association*, 48, 451–454 (Aug. 1959).

Wurster, D.E., "Preparation of Compressed Tablet Granulations by the Air–Suspension Technique II,", *Journal of the American Pharmaceuticl Association*, 49, 82–84 (Feb. 1960).

Pharmaceutical Sciences by Remington, 14$^{th}$ Ed., pp. 1626–1680 (1970), published by Mack Publishing Co.

Database WPI, Derwent Publication Ltd., London, GB, AN 94-031722, XP002096607.

Database WPI, Derwent Publication Ltd., London, GB, AN 94-068306, XP002096606.

Gupta, S.K. et al., "Evidence for Site–Specific Presystemic Metabolism of Oxybutynin Following Oral Administration," *Clinical Pharmacology & Therapeutics*, 61, 2, 1997, p. 227, XP002099744.

In the United States District Court for the Northern District of California, *Alza Corporation*, Plaintiff v. *Impax Laboratories*, Defendant, Case No. C–03–4032–VRW and C–03–4795, Decision Not to Dismiss California Declaratory Judgment Action, No Date.

IMPAX Notice of Paragraph IV Certification Letter regarding IMPAX Oxybutynin Chloride, 15 mg. Tablets w/Appendix, Jul. 25, 2003.

IMPAX Notice of Paragraph IV Certification Letter regarding IMPAX Oxybutynin Chloride, 5 and 10 mg. Tablets w/Appendix, Aug. 19, 2003.

In the United States District Court for the Northern District of California, Oakland Division, Case No. C–03–04032, Complaint for Patent Infringement w/Exhibit A, Sep. 4, 2003.

In the United States District Court for the Northern District of California, Oakland Division, Case No. C–03–04032, Answer, Affirmative Defenses and Counterclaims of IMPAX Laboratories, Inc., Oct. 1, 2003.

In the United States District Court for the Northern District of California, San Francisco Division, Case No. C–03–04032, Plaintiff ALZA Corporation's Reply to Defendant IMPAX Laboratories, Inc.'s Counterclaims, Nov. 13, 2003.

In the United States District Court for the Northern District of California, San Francisco Division, Case No. C–03–04032, IMPAX's Objections and Responses to Plaintiff's First Set of Interrogatories (Nos. 1–8), May 20, 2004.

In the United States District Court for the Northern District of California, Case No. C–03–4032 VRW, Order, No Date.

In the United States District Court, Northern District of California, San Francisco Division, Case No. C–03–04032, Plaintiff ALZA Corporation's Opening Memorandum of Law in Support of Claim Constructions, Dec. 15, 2004.

In the United States District Court for the Northern District of California, San Francisco Division, Case No. C–03–04032, IMPAX's Objections and Responses to Plaintiff's First Set of Interrogatories (Nos. 1–8), May 20, 2004.

In the United States District Court for the Northern District of California, Case No. C–03–4032 VRW, Order, No Date.

In the United States District Court, Northern District of California, San Francisco Division, Case No. C–03–04032, Plaintiff ALZA Corporation's Opening Memorandum of Law in Support of Claim Constructions, Dec. 15, 2004.

In the United States District Court, Northern District of California, San Francisco Division, Case No. C–03–04032, Declaration of Nicholas A. Peppas in Support of Plaintiff ALZA Corporation's Opening Memorandum of Law in Support of Claim Construction w/Exhibit A, Dec. 15, 2004.

In the United States District Court, Northern District of California, San Francisco Division, Case No. C–03–04032, Declaration of David Eiseman in Support of Plaintiff ALZA Corporation's Opening Memorandum of Law in Support of Claim Construction w/Exhibits A–F, Dec. 15, 2004.

In the United States District Court, Northern District of California, San Francisco Division, Case No. C–03–04032, Plaintiff ALZA Corporation's Objections and Responses to IMPAX Laboratories, Inc.'s First Set of Interrogatories, Jan. 10, 2005.

In the United States District Court, Northern District of California, San Francisco Division, Case No. C–03–04032, Plaintiff ALZA Corporation's Supplemental Opening Memorandum of Law in Support of Claim Construction w/Exhibits A–J, Jan. 13, 2005.

In the United States District Court, Northern District of California, San Francisco Division, Case No. C–03–04032, Defendant IMPAX Laboratories Inc.'s Responsive Claim Construction Brief, Mar. 10, 2005.

In the United States District Court, Northern District of California, San Francisco Division, Case No. C–03–04032, Declaration of Mark I. Koffsky in Support of Defendant IMPAX Laboratories Inc.'s Responsive Claim Construction Brief, w/Exhibits A–B, Mar. 10, 2005.

In the United States District Court, Northern District of California, San Francisco Division, Case No. C–03–04032, Declaration of Lewis J. Leeson in Support of Defendant IMPAX Laboratories Inc.'s Responsive Claim Construction Brief, w/Exhibit A, Mar. 10, 2005.

IMPAX Notice of Paragraph IV Certification Letter regarding IMPAX Oxybutynin Chloride 5, 10 and 15mg. (and patent validity)Tablets w/Appendix, Jul. 19, 2005.

In the United States District Court for the Northern District of West Virginia, *ALZA Corporation*, Plaintiff, v. *Mylan Laboratories, Inc. and Mylan Pharmaceutical, Inc.*, C.A. # 1:03CV61(Judge Keeley), Post trial Memorandum Opinion and Order, Sep. 27, 2005, 57 pages.

MYLAN Pharmaceuticals Inc. Notice of Paragraph IV Certification Letter regarding IMPAX Oxybutynin Chloride 10 mg. Tablets, Mar. 19, 2003.

In the United States District Court for the Northern District of West Virginia Clarksburg Office, Civil Action No. 1–03CV61, Complaint for Patent Infringement (ALZA) W/Exhibit A, May 2, 2003.

MYLAN Pharmaceuticals Inc. Notice of Paragraph IV Certification Letter regarding IMPAX Oxybutynin Chloride 5 mg. Tablets, May 21, 2003.

In the United States District Court for the Northern District of West Virginia Clarksburg Office, Civil Action No. 1–03CV61, Answer, Defenses and Counterclaims of Defendant Mylan Laboratories Inc., May 27, 2003.

In the United States District Court for the Northern District of West Virginia Clarksburg Office, Civil Action No. 1–03CV61, Reply to MYLAN Pharmaceuticals Inc.'s Counterclaims Filed in Consolidated Action 1:03CV158, Jul. 30, 2003.

In the United States District Court for the Northern District of West Virginia Clarksburg Office, Civil Action No. 1–03CV61, Mylan's Objections and Response to Plaintiff's First Set of Interrogatories, Sep. 18, 2003.

In the United States District Court for the Northern District of West Virginia Clarksburg Office, Civ. Action No. 1–03CV61, ALZA's Response to Mylan's First Set of Interrogatories, Sep. 29, 2003.

In the United States District Court for the Northern District of West Virginia Clarksburg Office, Civ. Action No. 1–03CV61, ALZA's Response to Mylan's Second Set of Interrogatories, Oct. 8, 2003.

In the United States District Court for the Northern District of West Virginia Clarksburg Office, Civ. Action No. 1–03CV61, ALZA's Response to Mylan's Third Set of Interrogatories, Dec. 18, 2003.

In the United States District Court for the Northern District of West Virginia Clarksburg Office, Civ. Action No. 1–03CV61, ALZA's Response to Mylan's Fourth Set of Interrogatories, Feb. 17, 2004.

In the United States District Court for the Northern District of West Virginia Clarksburg Office, Civil Action No. 1–03CV61, ALZA's Response to Mylan's Fifth Set of Interrogatories, Mar. 4, 2004.

In the United States District Court for the Northern District of West Virginia Clarksburg Office, Civil Action No. 1–03CV61, ALZA's Supplemental Response to Mylan's Fifth Set of Interrogatories (Interrogatory No. 12), Mar. 19, 2004.

In the United States District Court for the Northern District of West Virginia Clarksburg Office, Civil Action No. 1–03CV61, Mylan's Objections and Supplemental Responses to Plaintiff's first Set of Interrogatories, Mar. 21, 2004.

In the United States District Court for the Northern District of West Virginia Clarksburg Office, Civil Action No. 1–03CV61, ALZA's Second Supplemental Response to Mylan's Fifth Set of Interrogatories (Interrogatory No. 8), Mar. 26, 2004.

In the United States District Court for the Northern District of West Virginia Clarksburg Office, Civil Action No. 1–03CV61, ALZA's First Supplemental Response to Mylan's Third Set of Interrogatories (No. 6), Apr. 12, 2004.

In the United States District Court for the Northern District of West Virginia Clarksburg Office, Civil Action No. 1–03CV61, Mylan's Pretrial Memorandum, Dec. 2, 2004.

In the United States District Court for the Northern District of West Virginia Clarksburg Office, Civil Action No. 1–03CV61, Order Construing Claims and Denying Summary Judgment, Dec. 7, 2004.

In the United States District Court for the Northern District of West Virginia Clarksburg Office, Civil Action No. 1–03CV61, Plaintiff (ALZA's) Pre–Trial Memorandum (w/Exhibits A–C).

In the United States District Court for the Northern District of West Virginia Clarksburg Office, Civ. Action No. 1–03CV61, Markman Hearing Transcript, Dec. 29, 2004.

In the United States District Court for the Northern District of West Virginia Clarksburg Office, Civil Action No. 1–03CV61, Mylan's Notice Pursuant to 35 U.S.C. § 282, Jan. 7, 2005.

United States District Court for the Northern District of West Virginia Clarksburg Office, Civil Action No. 1–03CV61, Trial Transcript, Apr. 18, 2005.

In the United States District Court for the Northern District of West Virginia Clarksburg Office, Civil Action No. 1–03CV61, Mylan's Post–Trial Brief, with Exhibits A and B, May 6, 2005.

In the United States District Court for the Northern District of West Virginia Clarksburg Office, Civil Action No. 1–03CV61, Plaintiff (ALZA) Post–Trial Reply Memorandum, Jun. 1, 2005.

In the United States District Court for the Northern District of West Virginia Clarksburg Office, Civil Action No. 1–03CV61, Mylan's Post–Trial Reply Brief, Jun. 1, 2005.

Mylan Letter to Judge Irene M. Keely regarding ALZA's arguments in its Post Trial Reply Brief, 1 page, Jun. 15, 2005.

In the United States District Court for the Northern District of West Virginia Clarksburg Office, Civil Action No. 1–03CV61, Notice of Paragraph IV Certification US Patent 6,919,092 Oxybutynin Chloride Extended Release Tablets, 5 mg. and 10 mg. b, Jul. 22, 2005.

In the United States District Court for the Northern District of West Virginia Clarksburg Office, Civil Action No. 1–03CV61, Plaintiff (ALZA) Post–Trial Reply Memorandum (Corrected), No Date.

In the United States District Court for the Northern District of West Virginia, *Alza Corporation*, Plaintiff, V. *Mylan Laboratories, Inc.* Mylan Pharmaceuticals, Inc., Civil Action # 1:03CV61, Mylan's Supplemental Invalidity Contentions, Mylan's Supplemental Contentions Supporting the Invalidity of U.S. Patent No. 6,124,355, Jan. 29, 2003, 26 pages.

In the United States District Court for the Northern District of West Virginia, at Clarksburg, *Alza Corporation*, Plaintiff, V. *Mylan Laboratories, Inc. Mylan Pharmaceuticals, Inc.,* Civil Action # 1:03CV61, Mylan's Contentions Supporting the Invalidity of U.S. Patent No. 6,124,355, Dec. 29, 2003.

In the United States District Court for the Northern District of West Virginia, *Alza Corporation*, Plaintiff, V. *Mylan Laboratories, Inc. Mylan Pharmaceuticals, Inc.*, Civil Action # 1:03CV61, Mylan's Motion for Summary Judgment(#3) of Invalidity for Indefiniteness Under Honeywell, Jul. 14, 2004, 12 pages.

In the United States District Court for the Northern District of West Virginia, Clarksburg Office, *Alza Corporation*, Plaintiff, V. *Mylan Laboratories, Inc. Mylan Pharmaceuticals, Inc.*, Civil Action # 1:03CV61, Alza's Memorandum in Opposition to Defendant's Motion for Summary Judgment on Invalidity for Indefiniteness Under Honeywell (#3), Aug. 27, 2004, 15 pages.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Reply Memorandum in Support of its Motion for Summary Judgment (#3) of Invalidity for Indefiniteness Under Honeywell, Sep. 17, 2004, 14 pages.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Reply Memorandum in Support of its Motion for Partial Summary Judgment (#1) on the Threshold "Priority" Issue, With Attached Exhibit A, Jul. 14, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Reply Memorandum in Support of Its Motion for Summary Judgment (#2) of Invalidity based on Inherent Anticipation, Jul. 14, 2004, With attached Exhibits A & B.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Motion for Summary Judgment (#5) of Invalidity Based Upon a Lack of Novelty over the Prior Art, Memorandum in Support of Mylan's Motion for Summary Judgment (#5) of Invalidity Based upon a Lack of Novelty over the Prior Art, Jul. 14, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Alza's Memorandum in Opposition to Defendant's Motion for Summary Judgment (#5) of Invalidity based Upon a Supposed Lack of Novelty over the Prior Art, Aug. 27, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Reply Memorandum in Support of Its Motion for Summary Judgment (#5) of Invalidity Based Upon a Lack of Novelty over the Prior Art, Sep. 17, 2004, with attached Exhibits A, B.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Plaintiff Alza Corporation's Opening Memorandum of Law in Support of Claim Construction, Jul. 14, 2004, with attached Exhibits A thru I.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Plaintiff Alza Corporation's Memorandum in Reply to Defendants' Responsive Claim Constructin Memorandum, Sep. 3, 2004, with attached Exhibits N thru S.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Plaintiff Alza Corporation's Response to Defendants' "Markman" Claim Construction Memorandum, Aug. 20, 2004, with attached Exhibits J thru M.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's "Markman" Reply Memorandum, Sep. 3, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Reply Memorandum in Support of its Motion for Partial Summary Judgment (#1) on the Threshold "Priority" Issue, Sep. 3, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's "Markman" Claim Construction Memorandum, with attached Exhibits A thru C, Jul. 14, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Response to Alza's Claim Construction Memorandum, Aug. 20, 2004, with attached Exhibits A, B.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Motion for Summary Judgment (#2) of Invalidity Based on Inherent Anticipation, Jul. 14, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Motion for Partial Summary Judgment (#1) on the Threshold "Priority" Issue, Jul. 14, 2004, w/attached Exhibit A.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Motion for Summary Judgment (#5) of Invalidity based upon Lack of Novelty over the Prior Art, Jul. 14, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Alza's Combined Memorandum in Opposition to Defendant's Motion for Summary Judgment on the Threshold Priority Issue (#1) and Invalidity based on Inherent Anticipation, Aug. 20, 2004, with attached Exhibits A,B.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Mylan's Reply Memorandum in Support of Its Motion for Summary Judgment (#2) of Invalidity Based on Inherent Anticipation, Sep. 3, 2004.

In the United States District Court for the Northern District of West Virginia, Clarksburg Office, *Alza Corporation,* Plaintiff, V. *Mylan Laboratories, Inc. Mylan Pharmaceuticals, Inc.,* Civil Action # 1:03CV61, Plaintiff Alza Corporation's Memorandum in Reply to Defendant's Reponsive Claim Construction Memorandum, Sep. 7, 2004.

In the United States District Court for the Northern District of West Virginia, *Alza Corporation*, Plaintiff, V. *Mylan Laboratories, Inc. Mylan Pharmaceuticals, Inc.*, Civil Action # 1:03CV61, Mylan's Supplemental Briefing on Kennecott and Alleged "Inherent Written Description", Nov. 2, 2004.
In the United States District Court for the Northern District of West Virginia, *Alza Corporation*, Plaintiff, V. *Mylan Laboratories, Inc. Mylan Pharmaceuticals, Inc.*, Civil Action # 1:03CV61, Alza'a Memorandum in Response to Mylan's Supplemental Briefing on Kennecott and Alleged "Inherent Written Description", Nov. 13, 2004.
In the United States District Court for the Northern District of West Virginia, Clarksburg Office, *Alza Corporation*, Plaintiff, V. *Mylan Laboratories, Inc. Mylan Pharmaceuticals, Inc.*, Civil Action # 1:03CV61, Plaintiff's Pre–Trial Memorandum, Dec. 22, 2004.
In the United States District Court for the Northern District of West Virginia, Clarksburg Office, *Alza Corporation*, Plaintiff, V. *Mylan Laboratories, Inc. Mylan Pharmaceuticals, Inc.*, Civil Action # 1:03CV61, Mylan's Memorandum in Support of its Motion for Reconsideration, Dec. 23, 2004.
In the United States District Court for the Northern District of West Virginia, Clarksburg Office, *Alza Corporation*, Plaintiff, V. *Mylan Laboratories, Inc. Mylan Pharmaceuticals, Inc.,* Civil Action # 1:03V61, Mylan's Motion for Reconsideration of the Court's Ruling on Summary Judgments # 1 and #2, Dec. 24, 2004.
In the United States District Court for the Northern District of West Virginia, Clarksburg Office, *Alza Corporation*, Plaintiff, V. *Mylan Laboratories, Inc. Mylan Pharmaceuticals, Inc.*, Civil Action # 1:03CV61, Mylan's Motion for Reconsideration of the Court's Ruling on Summary Judgments #1 and #2, Mylan's Memorandum in Support of its Motion for Reconsideration, Jan. 24, 2005.
In the United States District Court for the Northern District of West Virginia, Clarksburg Office, *Alza Corporation*, Plaintiff, V. *Mylan Laboratories, Inc. Mylan Pharmaceuticals, Inc.*, Civil Action # 1:03CV61, Mylan's Reply Memorandum in Support of its Motion for Reconsideration, Jan. 31, 2005.
In the United States District Court for the Northern District of West Virginia, Clarksburg Office, *Alza Corporation*, Plaintiff, V. *Mylan Laboratories, Inc. Mylan Pharmaceuticals, Inc.*, Civil Action # 1:03CV61, Plaintiff's Post Trial Memorandum(Corrected) Jun. 1, 2005.
Ditropan XL NTS: Projections and Annuals, Defendant's Exhibit DX 2012.
Letter from Michael B. Chancellor, M.D. to Richard McCormick–Re: *ALZA*v. *Mylan* [Ditropan XL], Defendant's Exhibit DX 2016.
Quarterly TX Market Share (Updated), Defendant's Exhibit DX 2017.
Market Share Trends, Defendant's Exhibit DX 2018.
J & J Worldwide Advertising Group media Budget Control Record(MBCR), Ditropan, Defendant's Exhibit DX 2019.
DX 2020—Articles teaching that a Lower Dose of Oxybutynin is Effective and has Fewer Side Effects, Defendant's Exhibit DX 2020.
Ditropan XL: BMEs as a Percent of Net Trade Sales, Defendant's Exhibit DX 2024.

Alza Corporation Physician Advisory Board Meeting, Phoenix, AZ, 1998, Defendants Exhibit DX 2029.
Ditropan–Xl TRX Market Share Compared to Rebates (%NTS), Defendants Exhibit DX 2025.
Chancellor, M.B. MD., What is Really New in Overactive Bladder?, Feb. 25, 2004, Defendant's Exhibit DX 2038.
AWP Price Per Day: TID Oxy Products, Defendant's Exhibit 'S DX 2039.
Ditropan® Xl, Recommendation for Additional Clinical Study, Defendant's Exhibit 2056.
Ditropan XL: NTS Compared to Profits, Defendant's Exhibit DX 2061.
Ditropan XL Profits Compared to J & J Investment, Defendant's Exhibit DX 2062.
Ditropan XL Financial Data, Defendant's Exhibits DX 2063.
Ditropan–XL TRX Market Share Compared to BME/Selling (%NTS), Defendant's Exhibits DX 2065.
Ditropan Xl® vs Detrol® Spit Study, Post–Launch (Stage 5), Defendant's Exhibit DX 2067.
Physicians' Desk Reference, PDR®, 42 Edition, 1988, Ditropan Tablets and Syrup.
In the United States Court of Appeals for the Federal Circuit, *Alza Corporation*, Plaintiff, v. *Mylan Laboratories, Inc. and Mylan Pharmaceuticals, Inc.*, Defendants, *Alza Corporation* v. *Impax Laboratories, Inc.*, Defendant, Brief for Plaintiff–Appellant, Jan. 17, 2006, 1–69.
In the United States Court of Appeals for the Federal Circuit, *Alza Corporation,* Plaintiff, v. *Mylan Laboratories, Inc. and Mylan Pharmaceuticals, Inc.*, Defendants, *Alza Corporation* v. *Impax Laboratories, Inc.*, Defendant, Brief for Defendant–Appellee (IMPAX Laboratories, Inc.), Mar. 8, 2006, 1–32.
In the United States Court of Appeals for the Federal Circuit, *Alza Corporation*, Plaintiff, v. *Mylan Laboratories, Inc. and Mylan Pharmaceuticals, Inc.*, Defendants, *Alza Corporation* v. *Impax Laboratories, Inc.*, Defendant, Brief for Defendant–Appellee (Mylan Laboratories Inc. and Mylan Pharmaceuticals Inc.), Mar. 8, 2006, 1–65 and JA 20000–20088.
In the United States Court of Appeals for the Federal Circuit, *Alza Corporation,* Plaintiff, v. *Mylan Laboratories, Inc. and Mylan Pharmaceuticals, Inc.*, Defendants, *Alza Corporation* v. *Impax Laboratories, Inc.*, Defendant, Reply Brief for Plaintiff–Appellant, Apr. 3, 2006, 1–32.
In the United States District Court of Appeals for the Federal Circuit, *ALZA Corporation*, Plaintiff–Appellant, v. *Impax Laboratories, Inc.*, Defendant–Appellee, Decision–Judgment of Non–Infringement and Invalidity, Sep. 6, 2006, Appeal # 06–1047, 2 pages.
In the United States District Court of Appeals for the Federal Circuit, *ALZA Corporation*, Plaintiff–Appellant, v. *Mylan Laboratories, Inc. and Mylan Pharmaceuticals, Inc.*, Defendants–Appellees, Decision, Sep. 6, 2006, Appeal # 06–1019, 19 pages.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–23 are cancelled.

* * * * *